(12) United States Patent
Jun

(10) Patent No.: US 12,011,170 B2
(45) Date of Patent: Jun. 18, 2024

(54) BAND FOR SURGICAL WOUND SUTURE

(71) Applicant: Sungguen Jun, Eui Wang Si (KR)

(72) Inventor: Sungguen Jun, Eui Wang Si (KR)

(73) Assignee: Sungguen Jun, Eui Wang Si (KR)

( * ) Notice: Subject to any disclaimer, the term of this patent is extended or adjusted under 35 U.S.C. 154(b) by 0 days.

(21) Appl. No.: 18/350,167

(22) Filed: Jul. 11, 2023

(65) Prior Publication Data

US 2023/0346377 A1    Nov. 2, 2023

Related U.S. Application Data

(62) Division of application No. 16/763,398, filed as application No. PCT/KR2019/012376 on Sep. 24, 2019, now abandoned.

(30) Foreign Application Priority Data

Apr. 15, 2019    (KR) .................. 10-2019-0043711

(51) Int. Cl.
  *A61B 17/08*     (2006.01)
  *A61F 13/02*     (2024.01)

(52) U.S. Cl.
  CPC ........ *A61B 17/085* (2013.01); *A61F 13/0259* (2013.01); *A61B 2017/086* (2013.01)

(58) Field of Classification Search
  CPC ..... A61B 17/085; A61B 17/08; A61B 17/083; A61B 2017/086; A61B 2017/081; A61B 46/00; A61F 13/0246; A61F 13/0259; A61F 13/023; A61F 13/00085; A61F 2013/00553; A61F 2013/00561; A61F 2013/00817
  See application file for complete search history.

(56) References Cited

U.S. PATENT DOCUMENTS

| 4,696,301 | A | 9/1987 | Barabe |
| 2005/0020956 | A1 | 1/2005 | Lebner |
| 2005/0080453 | A1* | 4/2005 | Lebner ..................... B21L 3/00 |
| | | | 606/216 |
| 2005/0284801 | A1 | 12/2005 | Tacklind |

(Continued)

FOREIGN PATENT DOCUMENTS

| KR | 10-2014-0008536 A | 7/2015 |
| KR | 101564648 B1 | 10/2015 |
| KR | 101758236 B1 | 7/2017 |

*Primary Examiner* — Katherine H Schwiker
*Assistant Examiner* — Lauren Dubose
(74) *Attorney, Agent, or Firm* — Bridgeway IP Law Group, PLLC; Jihun Kim

(57) ABSTRACT

A band for surgical wound suture includes a first band having a first left band and a first right band and a second band located above the first band and having a second left band and a second right band, in which the first left band is connected to the second right band, and the second right band is connected to the first left band. The band for surgical wound suture provides advantages that an incision may be sutured by a simple operation of pulling the left and right bands to the left and right and attaching them, a feeling of heterogeneity after a suturing procedure may be minimized with a suturing device having a small volume and having almost no hard parts, and furthermore, the incision may be joined and firmly fixed by a wide and sturdy joint joined to both sides of the incision.

6 Claims, 27 Drawing Sheets

(56) References Cited

U.S. PATENT DOCUMENTS

2007/0038247 A1\* 2/2007 Lebner ................ A61B 17/085
                                                                606/215
2009/0281471 A1   11/2009 Iwahashi et al.
2018/0110658 A1    4/2018 Lin
2019/0046195 A1\*  2/2019 Belson ................ A61B 17/085
2021/0113208 A1\*  4/2021 Varadarajan ........ A61F 13/0236

\* cited by examiner

BAND FOR SURGICAL WOUND SUTURE

CROSS-REFERENCE TO RELATED APPLICATIONS

This application is a divisional application of the U.S. Utility patent application Ser. No. 16/763,398 filed on May 12, 2020, which is a national stage entry of PCT/KR2019/012376 filed on Sep. 24, 2019, which claims the priority of Korean Patent Application No. 10-2019-0043711 filed on Apr. 15, 2019, in the Korean Intellectual Property Office, the disclosure of which is incorporated herein by reference.

TECHNICAL FIELD

The present invention relates to a band for surgical wound suture, and more particularly, to a band for surgical wound suture including a first band having a first left band and a first right band and a second band located above the first band and having a second left band and a second right band.

BACKGROUND ART

In general, the human skin is an organ that covers the outside of the body and consists of three layers: the epidermal layer, the dermal layer, and the subcutaneous fat layer from the outside.

The epidermal layer of the skin is mostly occupied by keratinocytes, and the dermal layer is located under the epidermis, is made up of matricellular proteins such as collagen fibers and elastic fibers, and contains blood vessels, nerves, and sweat glands. In addition, the subcutaneous fat layer is made up of fat cells. Therefore, the skin comprehensively regulates body temperature and protects the body against the external environment.

When a cut wound that opens the dermal layer of the human skin from damages caused by unexpected accidents and carelessness in daily life is caused, or a wound that separates the skin from each other by surgery or bruise is caused, the wound is to be sutured immediately to prevent bacterial infection at the border of the laceration and to treat the skin cleanly and without scars.

Among the methods commonly used to close wounds caused by lacerations or surgical incisions on the skin, there are suturing and stapling. In both methods described above, there is a limitation in that trauma may remain during the suturing process of the wound.

The two methods described above may have a risk of infection not only for a patient, but also for a surgeon, which may cause blood-borne infection, and furthermore, may leave scars and have to visit the hospital again to remove sutures or staples.

The incision deeply penetrated into the tissue of the skin generally requires pulling the sides of the wound to promote healing and reduce scarring. Surgeons use a variety of suture techniques to minimize scarring during the healing process.

Since the above-mentioned suture techniques are closely related to the contamination of the wound, the suturing work should be done by a skilled medical practitioner. However, in the case of an emergency, immediate suturing by the skilled medical practitioner may be difficult. Even when the skilled medical practitioner directly performs the suturing, suturing of the incision during the immediate suturing may be difficult to be precisely performed, and in addition, contamination in the incision, for example, by bacteria, may be caused.

In order to solve the above-mentioned problems, Korean Patent Application No. 10-2014-0008536 (Title of Invention: Medical Wound Suturing Device) discloses a medical wound suturing device including an attachment part having a right attachment piece and a left attachment piece to be attached to the skin, a fixing portion having a right fixture and a left fixture vertically installed at each one end of the right and left attachment pieces of the attachment part, provided with a right fixing hole and a left fixing hole at the lower end of the inner side of the right and left fixtures, and having a right fixing piece and a left fixing piece elastically installed above the right and left fixing holes, and an adjustment portion having a fixing protrusion formed on the upper side of an adjustment piece to be inserted into the right and left fixing holes of the fixing part and be fixed by the right and left fixing pieces and having a hook piece at one end.

However, since the wound suturing device disclosed in the above patent document has a large volume and a large number of hard parts, there may be a problem in that severe heterogeneity is felt during the suturing procedure and in addition, the wound junction is narrowed and the wound is not adhered and firmly fixed.

A number of papers and patent documents are referenced and cited throughout this specification. The disclosures of cited papers and patent documents are incorporated herein by reference in their entirety, and the level of the technical field to which the present invention pertains and the content of the present invention are more clearly described.

DISCLOSURE OF THE INVENTION

Technical Problem

The inventors of the present invention have made efforts to develop a band for surgical wound suture capable of minimizing a feeling of heterogeneity after a suturing procedure with a suturing device having a small volume and having almost no hard parts, and furthermore, capable of adhering and firmly fixing an incision by a wide and sturdy joint joined to both sides of the incision.

Technical Solution

As a result, the present invention was completed by finding a fact that when a band for surgical wound suture is produced that includes a first band having a first left band and a first right band, and a second band located above the first band and having a second left band and a second right band, in which the first left band is connected to the second right band, and the second right band is connected to the first left band, an incision may be sutured by a simple operation of pulling the second left band and the second right band to the left and right and attaching them, a feeling of heterogeneity after a suturing procedure may be minimized with a suturing device having a small volume and having almost no hard parts, and furthermore, the incision may be adhered and firmly fixed by a wide and sturdy joint joined to both sides of the incision.

Advantageous Effects

The features and advantages of the present invention are summarized as follows:
(a) The present invention provides a band for surgical wound suture including a first band having a first left band and a first right band and a second band located above the first band and having a second left band and a second right band, in which the first left band is connected to the second right band, and the second right band is connected to the first left band.

(b) The band for surgical wound suture of the present invention provides advantages that an incision may be sutured by a simple operation of pulling the left and right bands to the left and right and attaching them, a feeling of heterogeneity after a suturing procedure may be minimized with a suturing device having a small volume and having almost no hard parts, and furthermore, the incision may be joined and firmly fixed by a wide and sturdy joint joined to both sides of the incision.

BEST MODE FOR CARRYING OUT THE INVENTION

Figure 1:
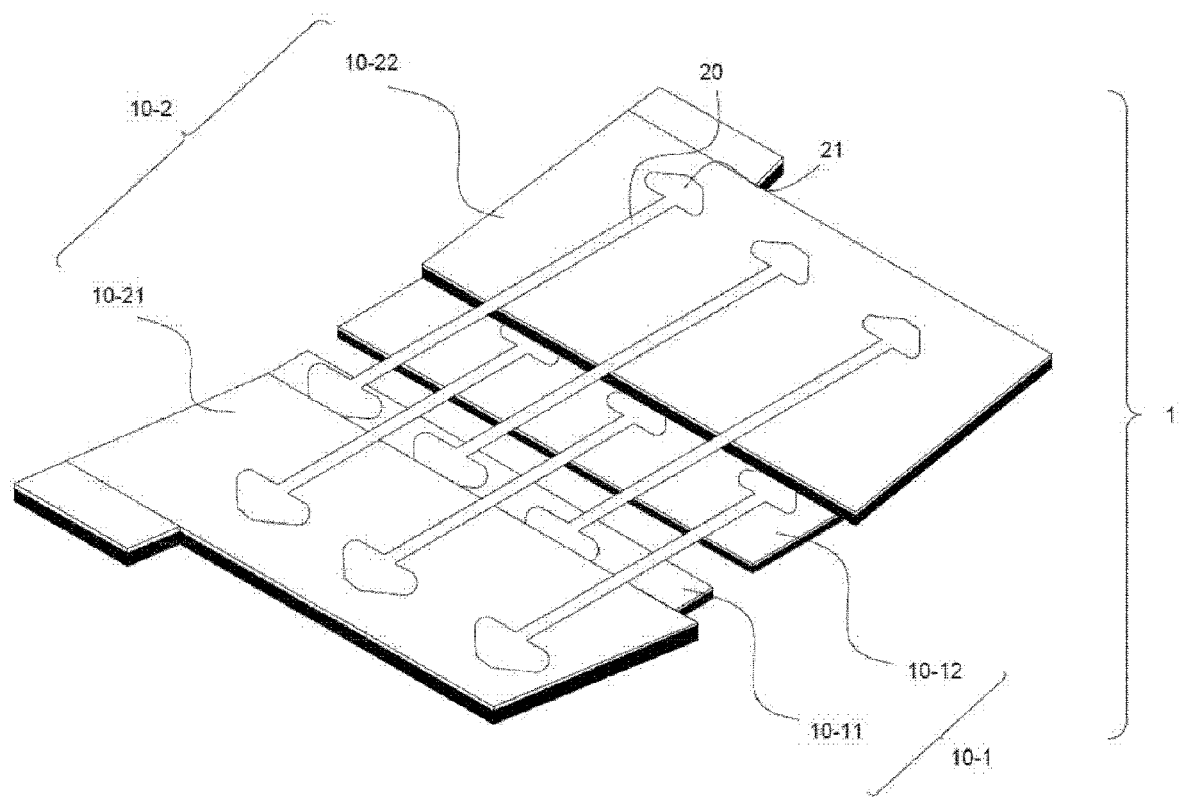
FIG. 1 is a perspective view showing a band for surgical wound suture of the present invention.
Figure 2:
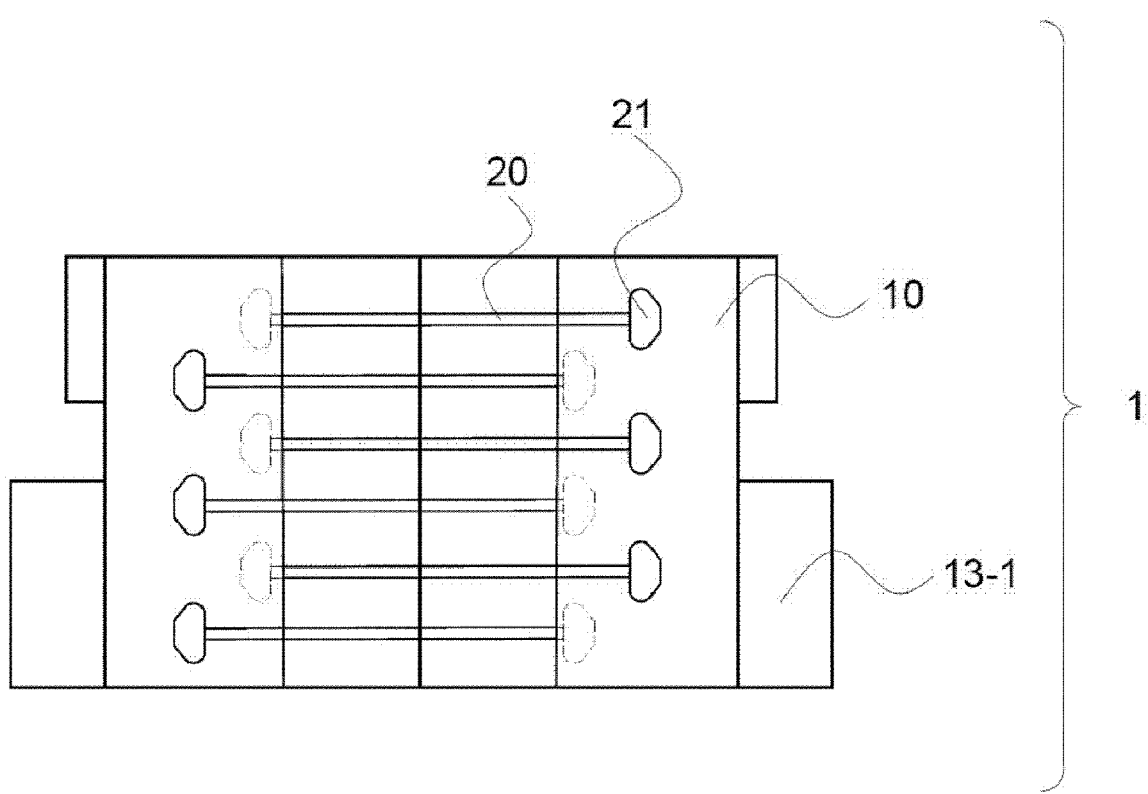
FIG. 2 is a front view showing the band for surgical wound suture of the present invention.

The present invention provides a band for wound suture.

The inventors of the present invention have made efforts to develop a band for surgical wound suture capable of minimizing a feeling of heterogeneity after a suturing procedure with a suturing device having a small volume and having almost no hard parts, and furthermore, capable of adhering and firmly fixing an incision by a wide and sturdy joint joined to both sides of the incision. As a result, a fact has been found that when a band for surgical wound suture is produced that includes a first band having a first left band and a first right band, and a second band located above the first band and having a second left band and a second right band, in which the first left band is connected to the second right band, and the second right band is connected to the first left band, an incision may be sutured by a simple operation of pulling the second left band and the second right band to the left and right and attaching them, a feeling of heterogeneity after a suturing procedure may be minimized with a suturing device having a small volume and having almost no hard parts, and furthermore, the incision may be adhered and firmly fixed by a wide and sturdy joint joined to both sides of the incision.

According to an aspect of the present invention, there is provided a band for surgical wound suture including a first band having a first left band and a first right band and a second band located above the first band and having a second left band and a second right band, in which the first left band is connected to the second right band, and the second right band is connected to the first left band.

The term "surgical wound" used in the present specification may mean any physical damage that has occurred to an organism such as a human and an animal.

The term "incision" used in the present specification may mean a cracked or opened state.

The term "suture" used in the present specification may mean any action that brings a cracked or opened state into a rejoined state.

The term "inner" used in the present specification is a relative concept and may mean a state located close to the center.

The term "outer" used in the present specification is a relative concept and may mean a state located farther from the center.

According to a preferred aspect of the present invention, the wound of the present invention may be preferably sutured by pulling the second left band and the second right band to the left and right.

The configuration of the present invention in which the wound is sutured by pulling the second left band and the second right band to the left and right is a very important configuration.

This is because, when the wound is sutured by pulling the second left band and the second right band to the left and right, there is no need for a separate surgical procedure for suturing, and furthermore, it is possible to minimize contamination and infection of the incision by minimizing contact of the incision with the outside.

According to a preferred aspect of the present invention, the band of the present invention may preferably include a support layer, an adhesive layer located under the support layer, and a release paper layer located under the adhesive layer.

According to a preferred aspect of the present invention, the release paper layer of the present invention may have an extension portion formed extending out of the support layer.

The configuration of the present invention in which the extension portion formed extending out of the support layer is provided on the release paper layer is a very important configuration. This is because it is convenient to remove the release paper layer when the extension portion is formed extending out of the support layer on the release paper layer, and furthermore, the extension portion may serve as a handle in the process of pulling the second band to the left and right.

According to a preferred aspect of the present invention, the adhesive band of the first left band and the adhesive layer of the first right band of the present invention may be preferably attached to one release paper layer.

The configuration of the present invention in which the adhesive layer of the first left band and the adhesive layer of the first right band are attached to one release paper layer is a very important configuration. This is because the first band and the second band are easily distinguished when the adhesive layer of the first left band and the adhesive layer of the first right band are attached to one release paper layer, and thus the first band and the second band can be quickly distinguished when an emergency and the like occurs.

According to a preferred aspect of the present invention, the release paper layer of the second band of the present invention may be preferably divided into an inner release paper and an outer release paper.

The configuration of the present invention in which the release paper layer of the second band is divided into the inner release paper and the outer release paper is a very important configuration. This is because, when the inner release paper is first removed among the release paper layer of the second band and attachment is performed, and then the outer release paper is removed and attachment is performed, it is possible to prevent the adhesive layer from being weakened by a hand or the like attached to the adhesive layer, and furthermore to minimize contamination and infection of the incision.

According to a preferred aspect of the present invention, the connection of the present invention may be preferably made by a connecting portion in which band attachment means are coupled or formed at both ends.

According to a preferred aspect of the present invention, preferably, one of the band attachment means may be coupled to the left band, and the other of the band attachment means may be coupled to the right band.

According to a preferred aspect of the present invention, the band for surgical wound suture of the present invention may preferably include a plurality of connecting portions, more preferably include one to ten connecting portions, even more preferably include two to five connecting portions, and most preferably include three connecting portions.

According to a preferred aspect of the present invention, the wound of the present invention may preferably be sutured by steps including the following:
  (a) removing the release paper of the first left band and the first right band;
  (b) attaching the first left band to the left of an incision;
  (c) attaching the first right band to the right of the incision;
  (d) removing the inner release papers of the second left band and the second right band;
  (e) pulling the second left band and the second right band to the left and right;
  (f) attaching the adhesive layers exposed by the removing of the inner release papers in the (d) to the first left band and the first right band, respectively; and
  (g) removing outer release papers of the second left band and the second right band, and then attaching the second left band and the second right band to the skin.

According to another aspect of the present invention, the present invention provides a medical skin suturing device including a first adhesive sheet and a second adhesive sheet respectively attached to skins on both sides on the basis of a suture, a first traction member having one end attached to the first adhesive sheet and the other end extending over the second adhesive sheet, a second traction member having one end attached to the second adhesive sheet and the other end extending over the first adhesive sheet, a first handle that is formed above the second adhesive sheet and to which the other end of the first traction member is attached, and a second handle that is formed above the first adhesive sheet and to which the other end of the second traction member is attached, in which an adhesive layer and a protective sheet are provided on the lower surfaces of the first and second handles.

According to a preferred aspect of the present invention, a plurality of the first traction members and the second traction members may be alternately arranged along the suture.

According to yet another aspect of the present invention, the present invention provides a medical skin suturing device including a first adhesive sheet and a second adhesive sheet respectively attached to skins on both sides on the basis of a suture, a first traction member having one end attached to the first adhesive sheet and the other end extending over the second adhesive sheet, a second traction member having one end attached to the second adhesive sheet and the other end extending over the first adhesive sheet, a first handle that is formed above the second adhesive sheet and to which the other end of the first traction member is attached, and a second handle that is formed above the first adhesive sheet and to which the other end of the second traction member is attached, in which the first traction member includes a first-first fixing portion attached to the first adhesive sheet, a first linear member extending from the first-first fixing portion toward the second adhesive sheet, and a first-second fixing portion formed at an end of the first linear member and attached to the first handle.

According to a preferred aspect of the present invention, the first-first fixing portion may be formed in a form in which a width is extended toward suture opposing edges inside the first adhesive sheet.

According to a preferred aspect of the present invention, the first-first fixing portion may be formed in a form in which a width is extended toward suture opposing edges inside the first adhesive sheet.

According to a preferred aspect of the present invention, the first linear member may be made of fiber yarn, and the first-first fixing portion and the first-second fixing portion may be synthetic resin materials, and be attached to both ends of the first linear member, respectively.

According to a preferred aspect of the present invention, the first linear member may include a first body part, one end of which extends to the first-second fixing portion, and a plurality of first branch portions branched from the other end of the first body part and extended to the first-first fixing portion.

According to a preferred aspect of the present invention, the first handle may include a first gripping portion formed to be spaced apart from the outside of the second adhesive sheet, and a first support that is formed to protrude from one edge of the first gripping portion and to which the first-second fixing portion is attached.

FORM FOR IMPLEMENTATION OF INVENTION

It is to be understood that the present invention may be variously modified and embodied, and thus particular embodiments thereof will be illustrated in the drawings and described in detail. However, this is not intended to limit the present invention to the specific embodiments, it should be understood to include all modifications, equivalents, and substitutes included in the spirit and scope of the present invention. In the description of the present invention, if it is determined that the detailed description of the known technology related to the present invention may unnecessarily obscure the subject matter of the present invention, the detailed description thereof will be omitted.

Hereinafter, preferable embodiments of the present invention will be described in detail with reference to the accompanying drawings.

First Embodiment

Figure 3:
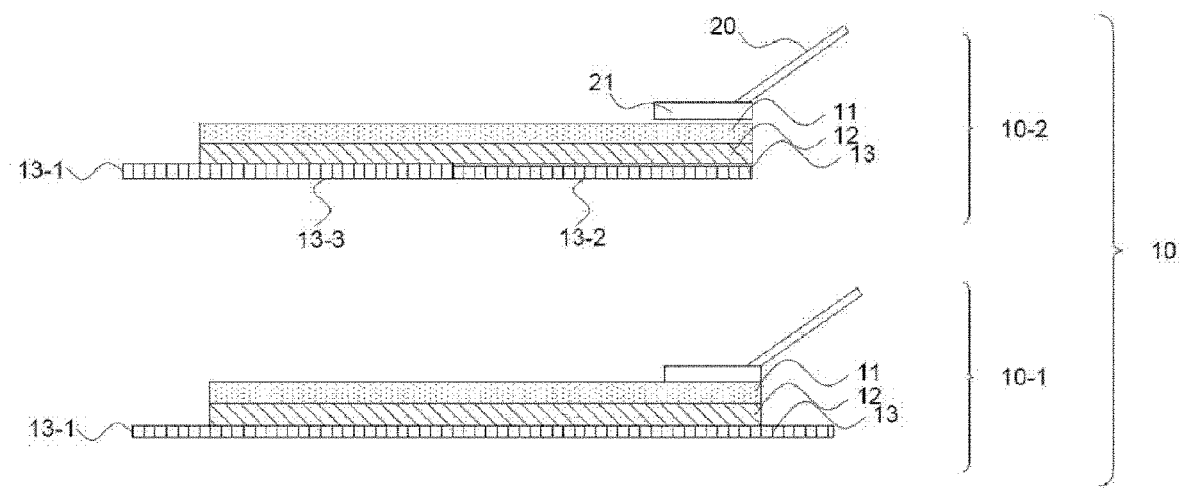
FIG. 3 is a cross-sectional view showing a cut portion of a left band part of the band for surgical wound suture of the present invention.
Figure 4:
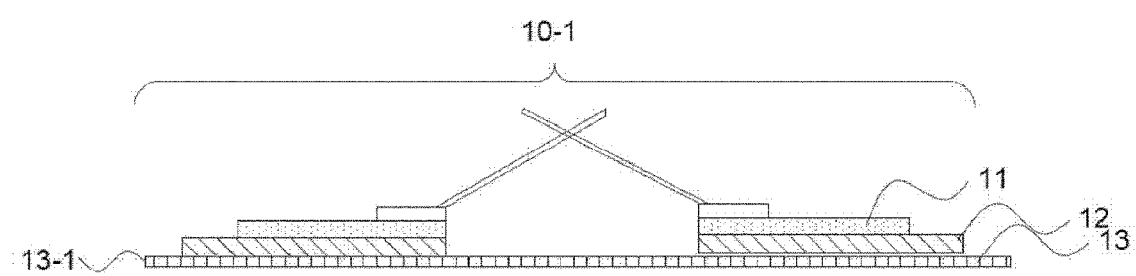
FIG. 4 is a cross-sectional view showing a cut portion of a first band part of the band for surgical wound suture of the present invention.
Figure 5:
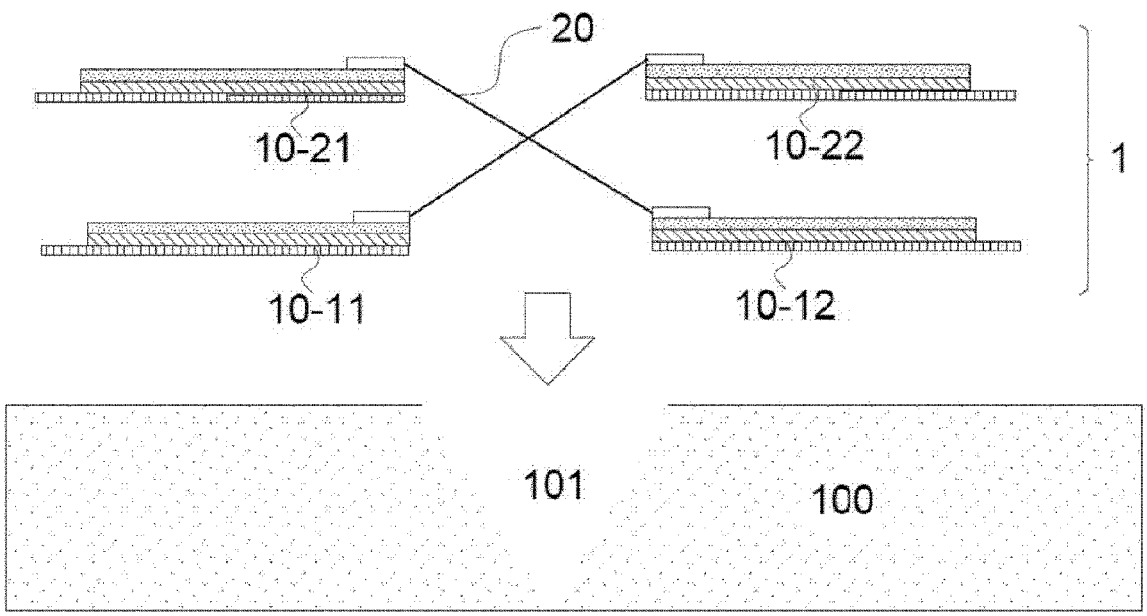
FIG. 5 is a use state diagram using a cross-sectional view of a cut portion of the band for surgical wound suture of the present invention.
Figure 6:
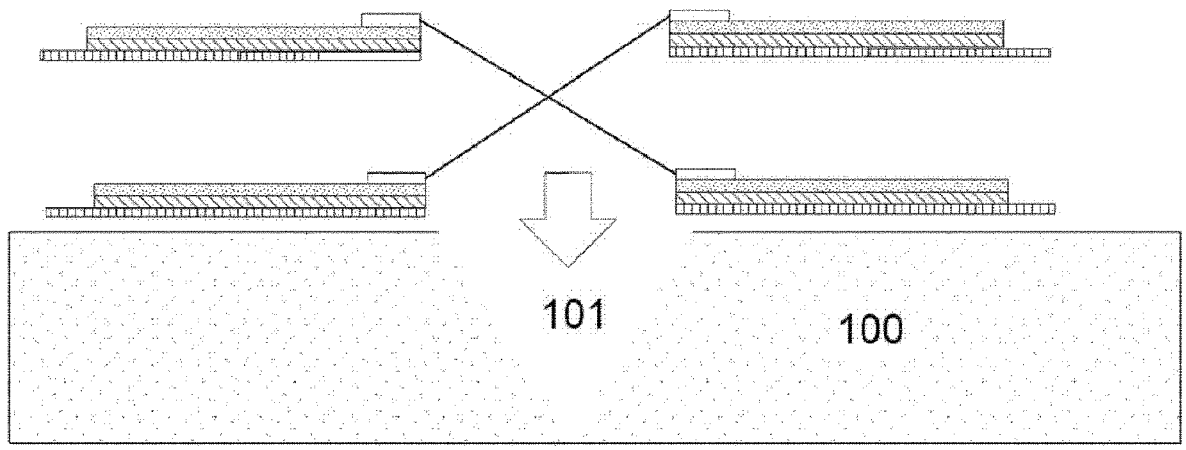
FIG. 6 is a use state diagram using a cross-sectional view of a cut portion of the band for surgical wound suture of the present invention.
Figure 7:
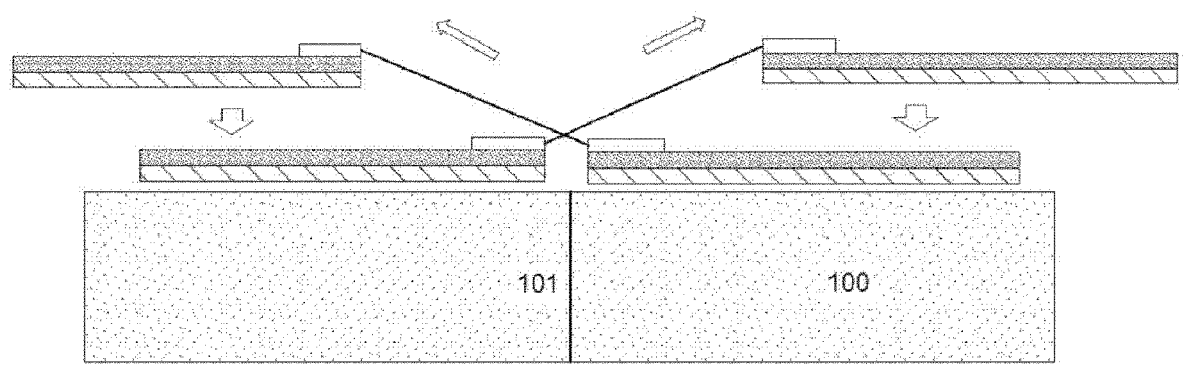
FIG. 7 is a use state diagram using a cross-sectional view of a cut portion of the band for surgical wound suture of the present invention.
Figure 8:
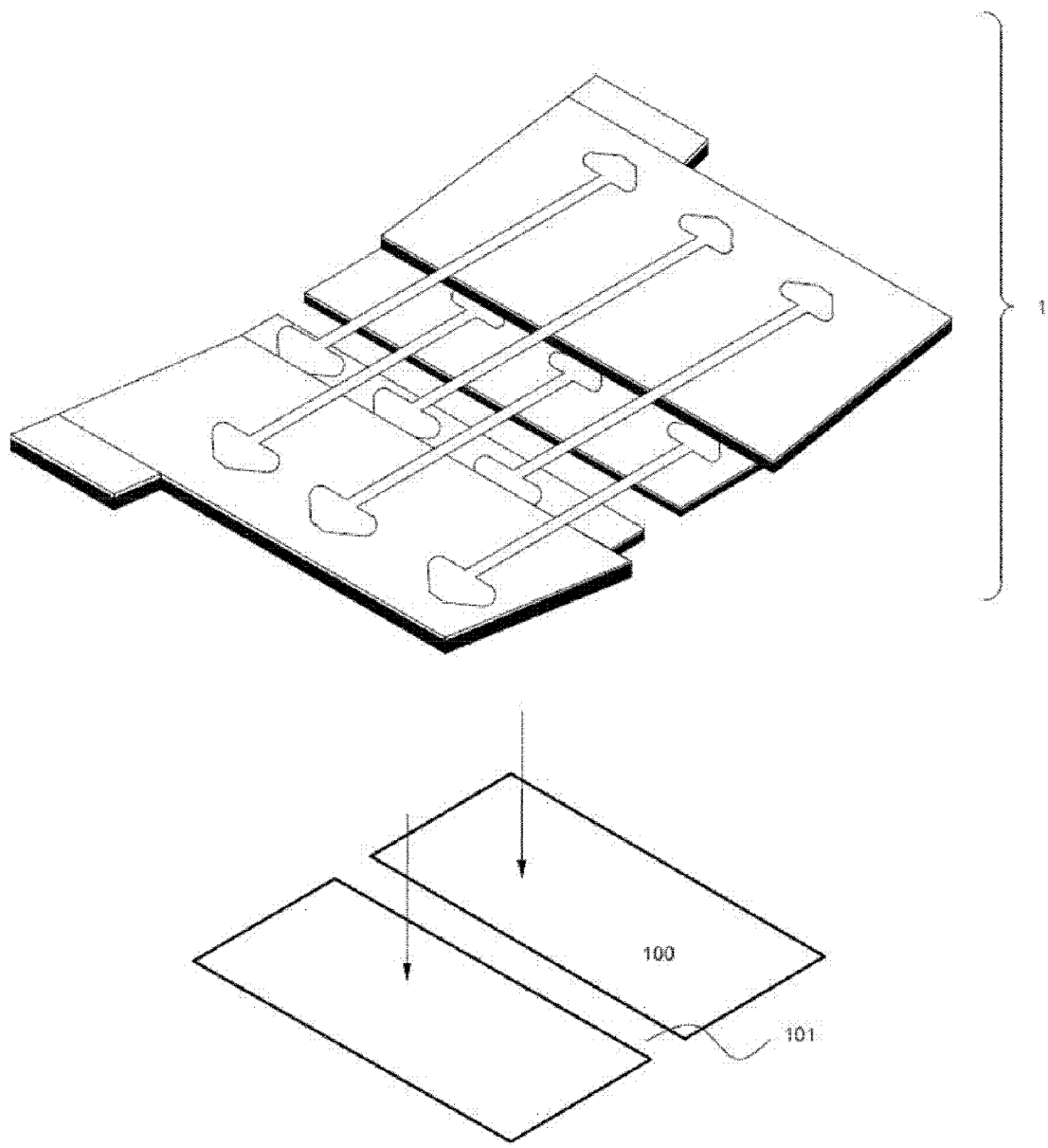
FIG. 8 is a use state diagram of the band for surgical wound suture of the present invention.
Figure 9:
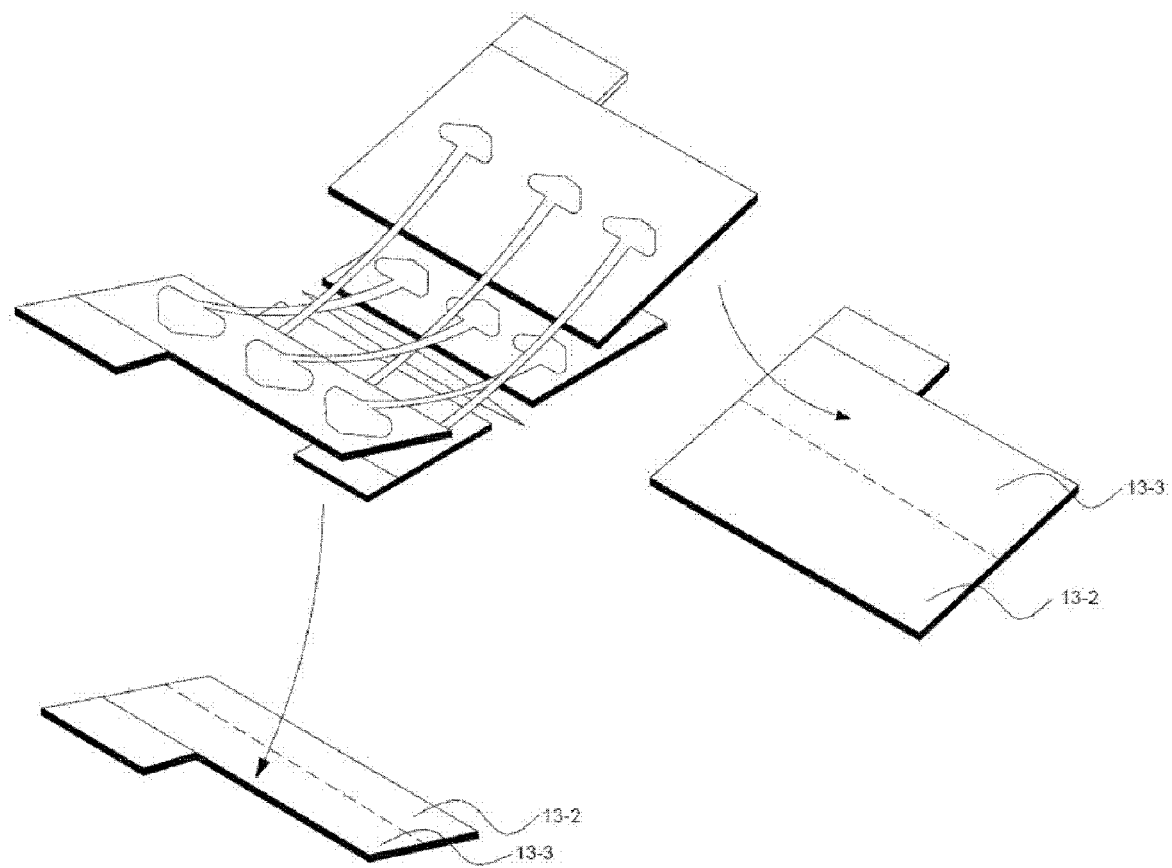
FIG. 9 is a use state diagram of the band for surgical wound suture of the present invention.
Figure 10:
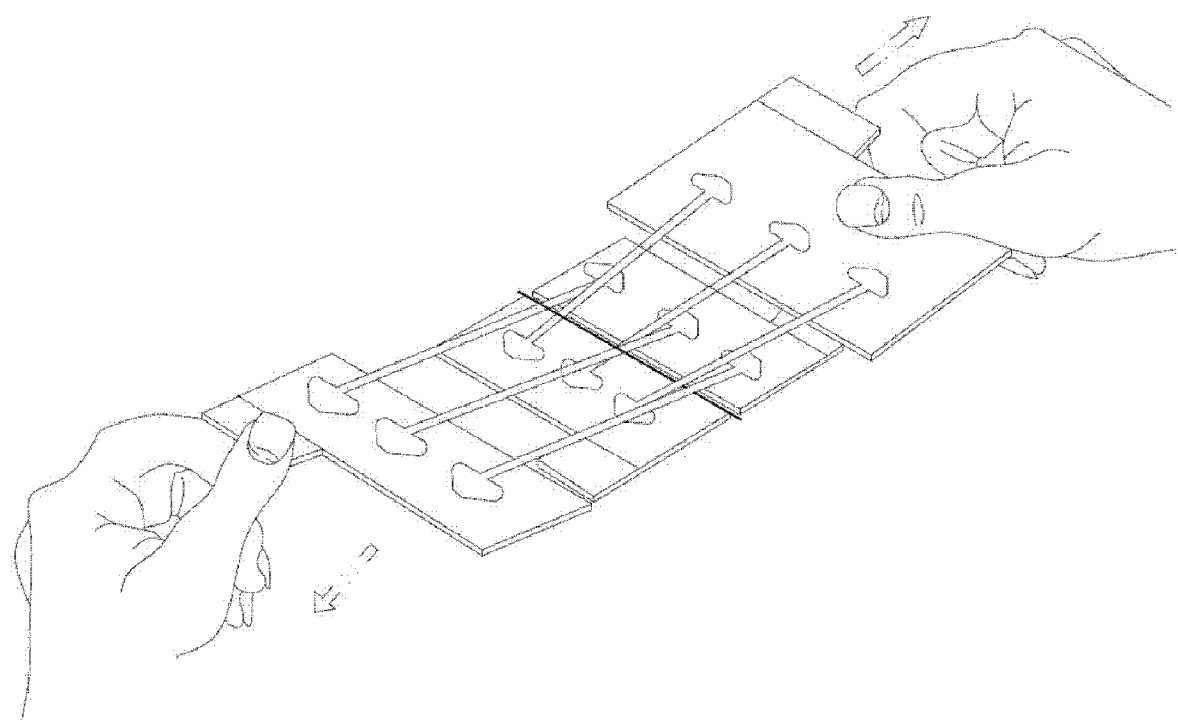
FIG. 10 is a use state diagram of the band for surgical wound suture of the present invention.

FIGS. 1 to 4 show a perspective view, a front view, a cross sectional view of a cut portion of a left band part, and a cross sectional view of a cut portion of a first band part, of a band 1 for surgical wound suture according to an embodiment of the present invention, FIGS. 5 to 7 show use state diagrams using a cross sectional portion of the band 1 for surgical wound suture according to an embodiment of the present invention, and FIGS. 8 to 10 show use state diagrams using a perspective view of the band 1 for surgical wound suture according to an embodiment of the present invention.

Referring to FIGS. 1 to 4, the band 1 for surgical wound suture according to an embodiment of the present invention is constituted by a support layer 11, an adhesive layer 12, and a release paper layer 13 including an extension portion 13-1, an inner release paper 13-2, and an outer release paper 13-3, and includes a first band 10-1 including a first left band 10-11 and a first right band 10-12, a second band 10-2 including a second left band 10-21 and a second right band 10-22, and a connecting portion 20 including band attachment means 21.

The band 1 for surgical wound suture according to an embodiment of the present invention is used to suture an incision site, that is, an incision 101, and, as shown in FIGS. 1 to 9, includes the first left band 10-11 and the first right band 10-12 that are adhered to both skins of the incision 101 on the basis of the incision 101, the second left band 10-21 and the second right band 10-22 for pulling the first left band 10-11 and the first right band 10-12 in a direction in contact with each other to close the incision 101, and an extension portion 13-1 provided outside first and second bands 10-1 and 10-2 such that the second left band 10-21 and the second right band 10-22 are pulled in opposite directions.

Referring to FIGS. 3 and 4, the band 10 according to an embodiment of the present invention is constituted by the support layer 11, the adhesive layer 12, and a release paper layer 13 including the extension portion 13-1, the inner release paper 13-2, and the outer release paper 13-3.

The support layer 11 corresponds to the main body of the band 10, has the adhesive layer 12 located under the support layer 11, and may be manufactured using a flexible elastic material used in the related art, for example, a flexible synthetic resin material.

The adhesive layer 12 serves to bond the support layer 11 to the skin or the top of band 10, has the release paper layer 13 located under the adhesive layer 12, and may be formed using various types of adhesives used in the related art.

The release paper layer 13 has the extension portion 13-1, the inner release paper 13-2, and the outer release paper 13-3.

The extension portion 13-1 is a portion formed by the release paper layer 13 extending out of the support layer 11, and serves to easily remove the release paper layer 13 from the support layer 11.

The inner release paper 13-2 is preferably applied only to the second band 10-2, and is a release paper located adjacent to the connecting portion 20 of the release paper layer 13.

The outer release paper 13-3 is preferably applied only to the second band 10-2, and is a release paper located next to the inner release paper 13-2 of the release paper layer 13.

Referring to FIGS. 1 to 4, the band 1 for surgical wound suture according to an embodiment of the present invention includes the first band 10-1 including the first left band 10-11 and the first right band 10-12, and the second band 10-2 including the second left band 10-21 and the second right band 10-22, and the connecting portion 20 including the band attachment means 21.

The first band 10-1 includes the first left band 10-11 and the first right band 10-12.

The first left band 10-11 is located under the second left band 10-21, is located to the left of the first right band 10-12, serves to be attached to the left skin of the incision 101, and is connected to the second right band 10-22 through a plurality of the connecting portions 20.

The first right band 10-12 is located under the second right band 10-22, is located to the right of the first left band 10-11, serves to be attached to the right skin of the incision 101, and is connected to the second left band 10-21 through the plurality of connecting portions 20.

The second band 10-2 includes the second left band 10-21 and the second right band 10-22.

The second left band 10-21 is located above the first left band 10-11, is located to the left of the second right band 10-22, serves to pull the first right band 10-12, and is connected to the first right band 10-12 through a plurality of connecting portions 20.

The second right band 10-22 is located above the first right band 10-12, is located to the right of the second left band 10-21, serves to pull the first left band 10-11, and is connected to the first left band 10-11 through a plurality of connecting portions 20.

The connecting portion 20 includes the linear member and the band attachment means 21 formed at both ends of the linear member.

The first left band 10-11 and the first right band 10-12 are formed in a sheet form having a predetermined area to be attached to both sides of the incision (101) on the basis of the incision 101, respectively, and have the adhesive layers 12 formed on the lower surface.

In addition, in order to protect the adhesive layer 12, the release paper layer 13 is attached to the lower side of the adhesive layer 12, and when used, the release paper layer 13 is removed and then the adhesive layer 12 is attached to the skin.

The first left band 10-11 and the first right band 10-12 are medical sheets and are to be firmly attached to the skin along the curved surface of the human body without lifting, and thus the first left band 10-11 and the first right band 10-12 may be made of elastic and flexible materials, such as flexible synthetic resin materials.

In addition, the first left band 10-11 and the first right band 10-12 may be sterilized, and a plurality of micro-pores may be formed for ventilation.

For example, the first left band 10-11 and the first right band 10-12 may be a hydrocolloid band used as a medical wet band.

Specifications such as widths and lengths of the first left band 10-11 and the first right band 10-12 may be appropriately selected depending on the size of the incision 101, and for this purpose, the band 1 for surgical wound suture according to the present invention may be prepared and provided in various specifications.

The second right band 10-22 and the second left band 10-21 serve to close the opened incision 101 by pulling the first left band 10-11 and the first right band 10-12 in directions in contact with each other.

To this end, the connecting portion 20 is disposed in an intersecting direction. That is, as shown in the figure, the second right band 10-22 and the first left band 10-11 are connected to each other by the connecting portion 20, the second left band 10-21, and the second right band 10-12 are connected to each other by the connecting portion 20.

Therefore, when the second right band 10-22 is pulled out of the first right band 10-12 and the second left band 10-21 is pulled out of the first left band 10-11, the first left band 10-11 is pulled in the direction toward the first right band 10-12 by the second right band 10-22, and the first right band 10-12 is pulled in the direction toward the first left band 10-11 by the second left band 10-21, and thus the distance between the first left band 10-11 and the first right band 10-12 is narrowed.

In this case, the skin attached to the first left band 10-11 is pulled in the direction toward the first right band 10-12, and the skin to which the first right band 10-12 is attached is pulled in the direction toward the first left band 10-11, and thus the skins on both sides of the incision 101 are brought into close contact with each other.

In addition, it is desirable that a plurality of connecting portions 20 are alternately formed in a zigzag form along the length direction of the first and second bands 10-1 and 10-2, for example, as shown in the figure, the connecting portions 20 may be alternately arranged one by one along the incision 101.

Meanwhile, the connecting portion 20 includes the linear member and the band attachment means 21 formed at both ends of the linear member.

The band attachment means 21 is formed on the upper surface of the band 10. The band attachment means 21 is for fixing one end of the linear member to the upper surface of the band 10, and may be, for example, a separate member to be distinguished from the band 10 such as an adhesive layer or adhesive tape for fixing one end of the linear member to the upper surface of the band 10.

As another example, when one end of the linear member is fused to the upper surface of the band 10, the band attachment means 21 refers to the fusion part of the linear member and the band 10.

As yet another example, when the band 10 and the linear member are integrally formed of the same material, the band attachment means 21 refers to a connecting portion between the band 10 and the linear member.

However, the present invention is not limited thereto, and the band attachment means 21 may have any configuration in which one end of the linear member is connected to the band 10.

The linear member according to an embodiment of the present invention is a linear member having a small width (or diameter or thickness) compared to a length, and may be a wire made of fiber or synthetic resin material.

For example, the linear member may be a fiber yarn such as a medical thread, or a string, strap, or tube made of synthetic resin material.

In this case, it is also possible that the band attachment means 21 and the linear member are integrally formed of the same synthetic resin material.

When the linear member is made of the fiber yarn, the band attachment means 21 which are both ends of the linear member may be attached to the band 10 by medical adhesives or the like.

In the band 1 for surgical wound suture according to an embodiment of the present invention, when attached to the incision 101, the linear members cross over the incision 101.

In this case, as the linear member is a thin thread or wire, a significant portion of the incision 101 is exposed to the space between the linear members, and thus a follow-up treatment such as disinfection is made easy.

The second right band 10-22 and the second left band 10-21 serve as handles for pulling the first left band 10-11 and the first right band 10-12, respectively, and are formed on the first right band 10-12 and the first left band 10-11, respectively.

It is desirable that the second right band 10-22 and the second left band 10-21 are formed with an area that is easily gripped by a user.

Referring to FIGS. 5 to 10, the band 1 for surgical wound suture according to an embodiment of the present invention may be used in the following method:

(a) removing the release paper layer 13 of the first left band 10-11 and the first right band 10-12;
(b) attaching the first left band 10-11 to the left of the incision 101;
(c) attaching the first right band 10-12 to the right of the incision 101;
(d) removing the inner release papers 13-2 of the second left band 10-21 and the second right band 10-22;
(e) pulling the second left band 10-21 and the second right band 10-22 to the left and right;
(f) attaching the adhesive layers exposed by the removing of the inner release papers 13-2 in the (d) to the first left band 10-11 and the first right band 10-12, respectively; and
(g) removing outer release papers 13-3 of the second left band 10-21 and the second right band 10-22, and then attaching the second left band 10-21 and the second right band 10-22 to the skin.

FIGS. 5 to 10 are use state diagrams of the band 1 for surgical wound suture according to an embodiment of the present invention, and a method of using a medical skin suturing device according to an embodiment of the present invention will be described in detail below with reference to the drawings.

First, as shown in FIGS. 5 to 10, the release paper layers 13 of the first left band 10-11 and the first right band 10-12 are removed, and the first left band 10-11 and the first right band 10-12 are attached to both skins of the incisions 101 on the basis of the incision 101.

Next, the release paper layers 13 are removed from the second right band 10-22 and the second left band 10-21.

In this case, for the release paper layer 13 of the second band 10-2, the inner release paper 13-2 is first removed to attach the second band 10-2 to the outer portion of the first band 10-1, and then the outer release paper 13-3 is removed and attached.

Here, when the inner release paper is first removed, of the release paper layer 13 of the second band 10-2, and attachment is performed, and then the outer release paper 13-3 is removed and attachment is performed, it is possible to prevent the adhesive layer from being weakened by a hand or the like attached to the adhesive layer, and furthermore to minimize contamination of the incision 101.

The same release paper layer 13 is attached to the first right band 10-12 and the first left band 10-11, such that the release paper layer 13 is removed at a time.

On the other hand, separate release paper layers 13 are attached to the second right band 10-22 and the second left band 10-21, and in this case, the release paper layers 13 are to be separately removed.

Next, the second right band 10-22 is pulled out of the first right band 10-12, and the second left band 10-21 is pulled out of the first left band 10-11.

In this process, the second right band 10-22 pulls the first left band 10-11, and the second left band 10-21 pulls the first right band 10-12, and thus the skins on both sides of the incision 101, to which the first left band 10-11 and the first right band 10-12 are attached respectively, get closed to each other while narrowing the gap, and then come into contact and sutured.

Then, in a state where the incision 101 is sutured, the second right band 10-22 and the second left band 10-21 are attached to the first left band 10-11 and the skin and the first right band 10-12 and the skin.

With the band 1 for surgical wound suture according to an embodiment of the present invention, as the linear member is a thin thread or a string made of a synthetic resin material, a significant portion of the incision 101 is exposed between the linear members.

Therefore, even after the procedure of the band 1 for surgical wound suture, a follow-up treatment such as disinfection for the incision 101 is made easy as shown in FIG. 10.

Second Embodiment

Figure 11:
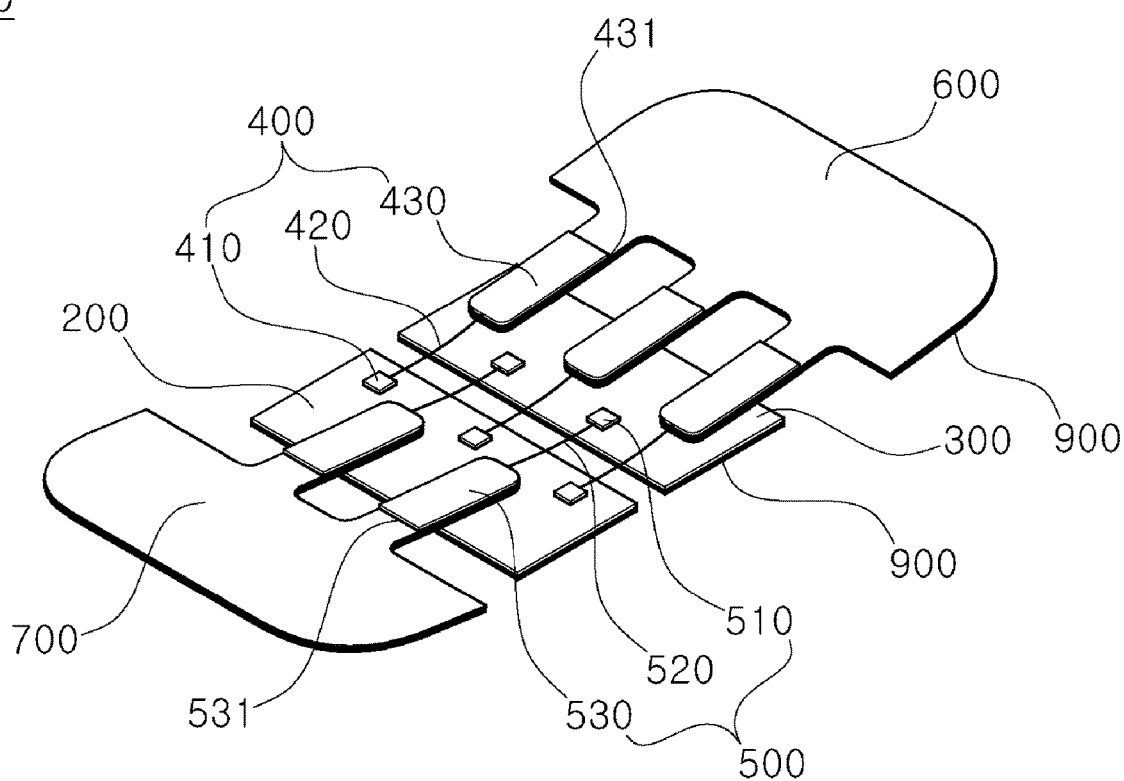
FIG. 11 is a perspective view showing a medical skin suturing device according to a first embodiment of the present invention.
Figure 12:
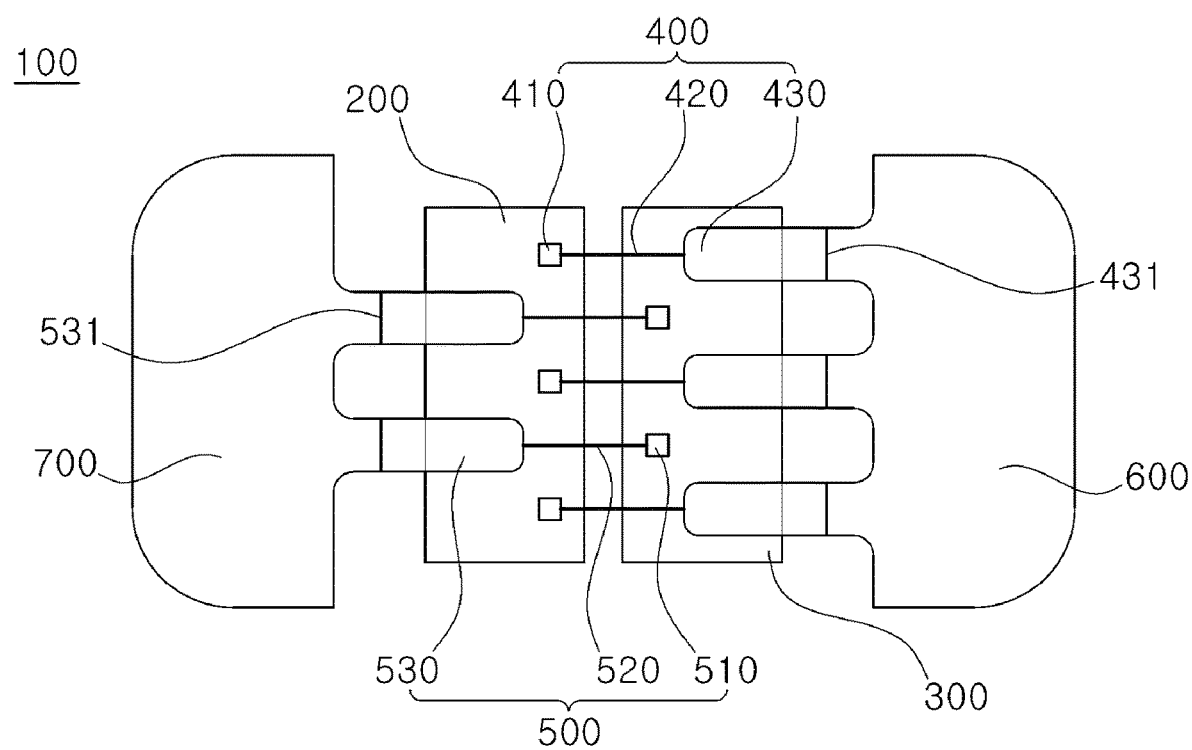
FIG. 12 is a plan view showing the medical skin suturing device according to the first embodiment of the present invention.
Figure 13:
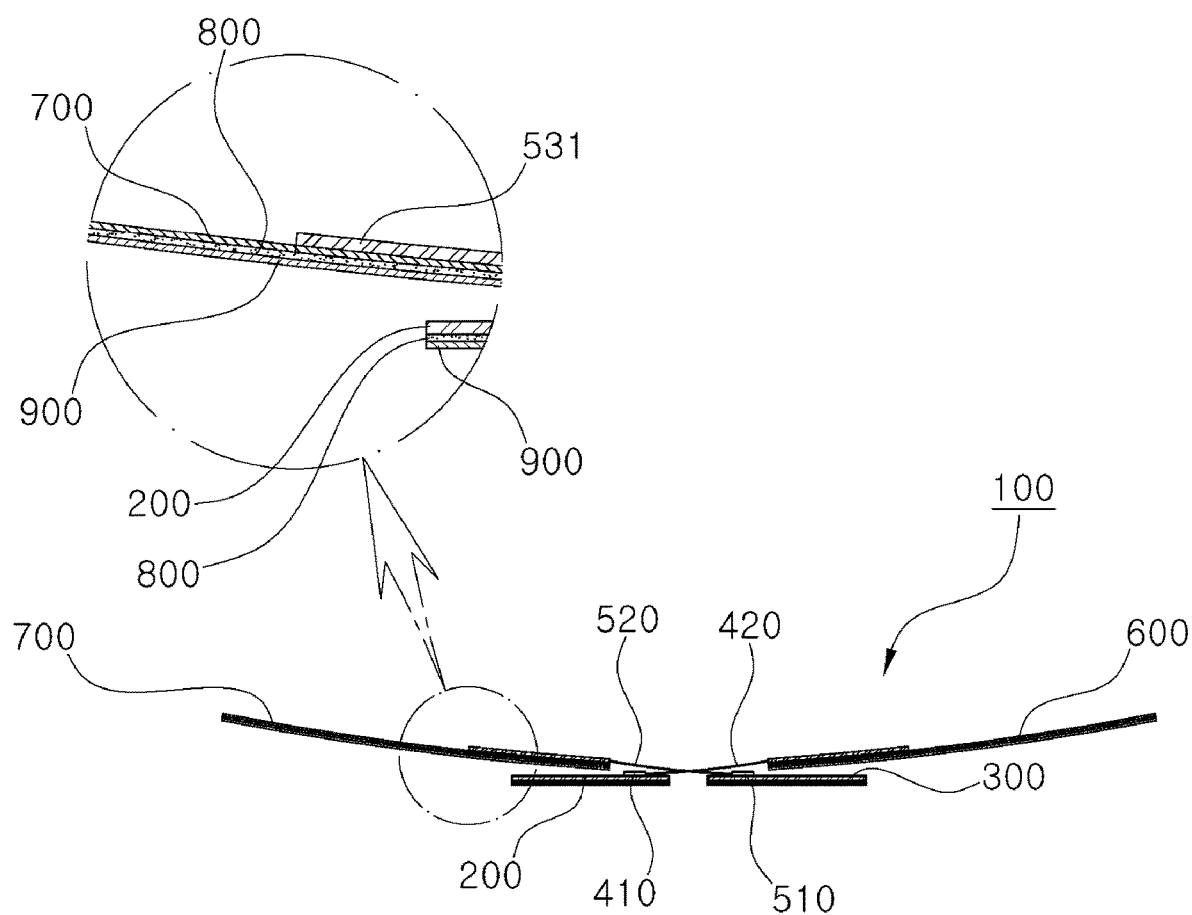
FIG. 13 is a cross-sectional view showing the medical skin suturing device according to the first embodiment of the present invention.

FIG. 11 is a perspective view showing a medical skin suturing device according to a first embodiment of the present invention, FIG. 12 is a plan view showing the medical skin suturing device according to the first embodiment of the present invention, and FIG. 13 is a cross-sectional view showing the medical skin suturing device according to the first embodiment of the present invention.

The medical skin suturing device 100 according to the first embodiment of the present invention is used to suture an incision site, that is, a suture (see FIG. 25), and, as shown in FIGS. 11 to 13, includes a pair of first and second adhesive sheets 200 and 300 that are adhered to the skins on both sides of the suture on the basis of the suture, first and second traction members 400 and 500 for pulling the first and second adhesive sheets 200 and 300 in a direction in contact with each other to close the suture, and first and second handles 600 and 700 provided outside the first and second adhesive sheets 200 and 300 such that the first and second traction members 400 and 500 are pulled in opposite directions.

The first adhesive sheet 200 and the second adhesive sheet 300 are formed in a sheet form having a predetermined area to be attached to both sides of the suture, on the basis of the suture, respectively, and have adhesive layers 800 (see FIG. 13) formed on the lower surfaces thereof. In addition, in order to protect the adhesive layer 800, a protective sheet 900 is attached to the lower side of the adhesive layer 800, and when used, the protective sheet 900 is removed and then the adhesive layer 800 is attached to the skin.

The first adhesive sheet 200 and the second adhesive sheet 300 are medical sheets and are to be firmly attached to the skin along the curved surface of the human body without lifting, and thus the first adhesive sheet 200 and the second adhesive sheet 300 may be made of elastic and flexible materials, such as flexible synthetic resin materials. In addition, the first adhesive sheet 200 and the second adhesive sheet 300 may be sterilized, and a plurality of micropores may be formed for ventilation. As an example, the first adhesive sheet 200 and the second adhesive sheet 300 may be a hydrocolloid band used as a medical wet band.

Specifications such as widths and lengths of the first adhesive sheet 200 and the second adhesive sheet 300 may be appropriately selected depending on the size of the suture, and for this purpose, the medical skin suturing device 100 according to the present invention may be prepared and provided in various specifications.

The first traction member 400 and the second traction member 500 each pull the first adhesive sheet 200 and the second adhesive sheet 300 in a direction in contact with each other, and serve to close the opened suture. To this end, the first and second traction members 400 and 500 are arranged in opposite directions. That is, as shown in the figure, the first traction member 400 has one end fixed to the first adhesive sheet 200 and the other end extending over and beyond the second adhesive sheet 300, and the second traction member 500 has one end fixed to the second adhesive sheet 300 and the other end extending over and beyond the first adhesive sheet 200.

Therefore, when the first traction member 400 is pulled out of the second adhesive sheet 300 and the second traction member 500 is pulled out of the first adhesive sheet 200, the first adhesive sheet 200 is pulled in the direction toward the second adhesive sheet 300 by the first traction member 400, the second adhesive sheet 300 is pulled in the direction toward the first adhesive sheet 200 by the second traction member 500, and thus the gap between the first and second adhesive sheets 200 and 300 is narrowed. In this case, the skin to which the first adhesive sheet 200 is attached is pulled in the direction toward the second adhesive sheet 300, the skin to which the second adhesive sheet 300 is attached is pulled in the direction toward the first adhesive sheet 200, and thus the skins on both sides of the suture are brought into close contact with each other.

In addition, it is desirable that a plurality of first and second traction members 400 and 500 are alternately formed in a zigzag form along the length direction of the first and second adhesive sheets 200 and 300, for example, as shown in the figure, the first traction member 400 and the second traction member 500 may be alternately arranged one by one along the suture. In this case, it is desirable to uniformly apply the traction force by the first and second traction members 400 and 500 to the first and second adhesive sheets 200 and 300 such that the first and second adhesive sheets 200 and 300 are not twisted to one side in the process of pulling the first and second traction members 400 and 500, and for this purpose, it is desirable to dispose the first and second traction members 400 and 500 in different numbers from each other. For example, as shown in the figure, there may be one more first traction members 400 disposed than the second traction members 500, or conversely, there may be one more second traction members 500 disposed than the first traction members 400.

On the other hand, the first traction member 400 includes a first-first fixing portion 410, a first linear member 420, and a first-second fixing portion 430, and the second traction member 500 Includes a second-first fixing portion 510, a second linear member 520, and a second-second fixing portion 530. The first-first fixing portion 410 and the second-first fixing portion 510, the first linear member 420 and the second linear member 520, and the first-second fixing portion 430 and the second-second fixing portion 530 have the same configurations in pairs, and therefore the first traction member 400 will be described in detail below by way of example.

The first-first fixing portion 410 is formed on the upper surface of the first adhesive sheet 200. The first-first fixing portion 410 is for fixing one end of the first linear member 420 to the upper surface of the first adhesive sheet 200, and may be, for example, a separate member to be distinguished from the first adhesive layer 200 such as an adhesive layer or adhesive tape for fixing one end of the first linear member 420 to the upper surface of the first adhesive sheet 200. As another example, when one end of the first linear member 420 is fused to the upper surface of the first adhesive sheet 200, the first-first fixing portion 410 refers to the fusion portion of the first linear member 420 and the first adhesive sheet 200. As yet another example, when the first adhesive sheet 200 and the first linear member 420 are integrally formed of the same material, the first-first fixing portion 410 refers to a connecting portion between the first adhesive sheet 10 and the first linear member 420. However, the present invention is not limited thereto, and the first-first fixing portion 410 may have any configuration in which one end of the first linear member 420 is connected to the first adhesive sheet 200.

The first linear member 420 has one end fixed to the first-first fixing portion 410 and the other end extending toward the second adhesive sheet 300.

The first linear member 420 according to the first embodiment of the present invention is a linear member having a small width (or diameter or thickness) compared to a length, and may be a wire made of fiber or synthetic resin material. For example, the first linear member 420 may be a fiber yarn such as a medical thread, or a string, strap, or tube made of synthetic resin material. In this case, it is also possible that the first-first fixing portion 410 and the first linear member 420 are integrally formed of the same synthetic resin material. When first the linear member 420 is the fiber yarn, both ends of the first linear member 420 may be attached to the first-first fixing portion 410 and the first-second fixing portion 430, respectively, by medical adhesives or the like.

The first-second fixing portion 430 applies a traction force to the first linear member 420 while supporting the tension applied to the first linear member 420, with one end thereof being fixed to the other end of the first linear member 420 and the other end being fixed to the first handle 600. As an example, the first-second fixing portion 430 may be a hydrocolloid band used as a medical wet band, and the adhesive layer 800 is formed on the lower surface of the first-second fixing portion 430 and the protective sheet 900 is attached to the lower portion of the adhesive layer 800. The protective sheet 900 of the first-second fixing portion 430 may be integrally formed with the protective sheet 900 of the first handle 600 to be described later. The other end of the first linear member 420 may be fixed to one side of the first-second fixing portion 430 by a method such as adhesion or fusion, and the other end of the first linear member 420 may also be coupled and fixed to one side of the second-second fixing portion 530 by a separate member. Meanwhile, it is also possible that the first linear member 420 and the first-second fixing portion 430 are integrally formed of the same material. For example, the first-second fixing portion 430 has the same material as the first linear member 420, and may be integrally formed with the first linear member 420.

When the medical skin suturing device 100 according to the first embodiment of the present invention is attached to the suture, the first linear member 420 and the second linear member 520 cross over the suture. In this case, as the first and second linear members 420 and 520 are a thin thread or wire, a significant portion of the suture is exposed to the space between the first and second linear members 520s, and thus a follow-up treatment such as disinfection is made easy.

Therefore, it is desirable that one end of the first-second fixing portion 430, to which the other end of the first linear member 420 is fixed, moves to the outside of the suture during the suturing procedure, and enters the inside of the second adhesive sheet 300 such that the first-second fixing portion 430 which is wider than the first linear member 420 does not cover the suture.

The first handle 600 and the second handle 700 serve as handles for pulling the first traction member 400 and the second traction member 500, respectively, and are formed outside and upward of the second adhesive sheet 300 and the first adhesive sheet 200, respectively. It is desirable that the first handle 600 and the second handle 700 are formed with an area that is easily gripped by a user. As an example, the first and second handles 600 and 700 may be formed of the same material as the first and second adhesive sheets 200 and 300 described above.

The other end of the first-second fixing portion 430 is fixed to one side of the first handle 600, and the other end of the second-second fixing portion 530 is fixed to one side of the second handle 700. As an example, the other ends of first and second supports 430 and 530 may be attached to the upper surfaces of the first and second handles 600 and 700 by adhesive or fusion.

As another example, the first handle 600 and the second handle 700 may include a gripping portion formed with a predetermined area, and a plurality of supports protruding and facing the first-second fixing portion 430 or the second-second fixing portion 530 at one edge of the gripping portion. In this case, the first-second fixing portion 430 and the second-second fixing portion 530 may be attached to the upper surfaces of the supports by adhesive or fusion.

As another example, it is possible that the first-second fixing portion 430 and the first handle 600, and the second-second fixing portion 530 and the second handle 700 are integrally formed of the same material.

The lower surfaces of the first and second handles 600 and 700 are provided with the adhesive layers 800 and the protective sheets 900, and the same protective sheet 900 may be attached to the lower surfaces of the first handle 600 and the first-second fixing portion 430, and the same protective sheet 900 may be attached to the lower surfaces of the second handle 700 and the second-second fixing portion 530.

FIGS. 14 to 20 are use state diagrams of the medical skin suturing device 1 according to the first embodiment of the present invention, and a method of using a medical skin suturing device according to the first embodiment of the present invention will be described in detail below with reference to the drawings.

Figure 14:
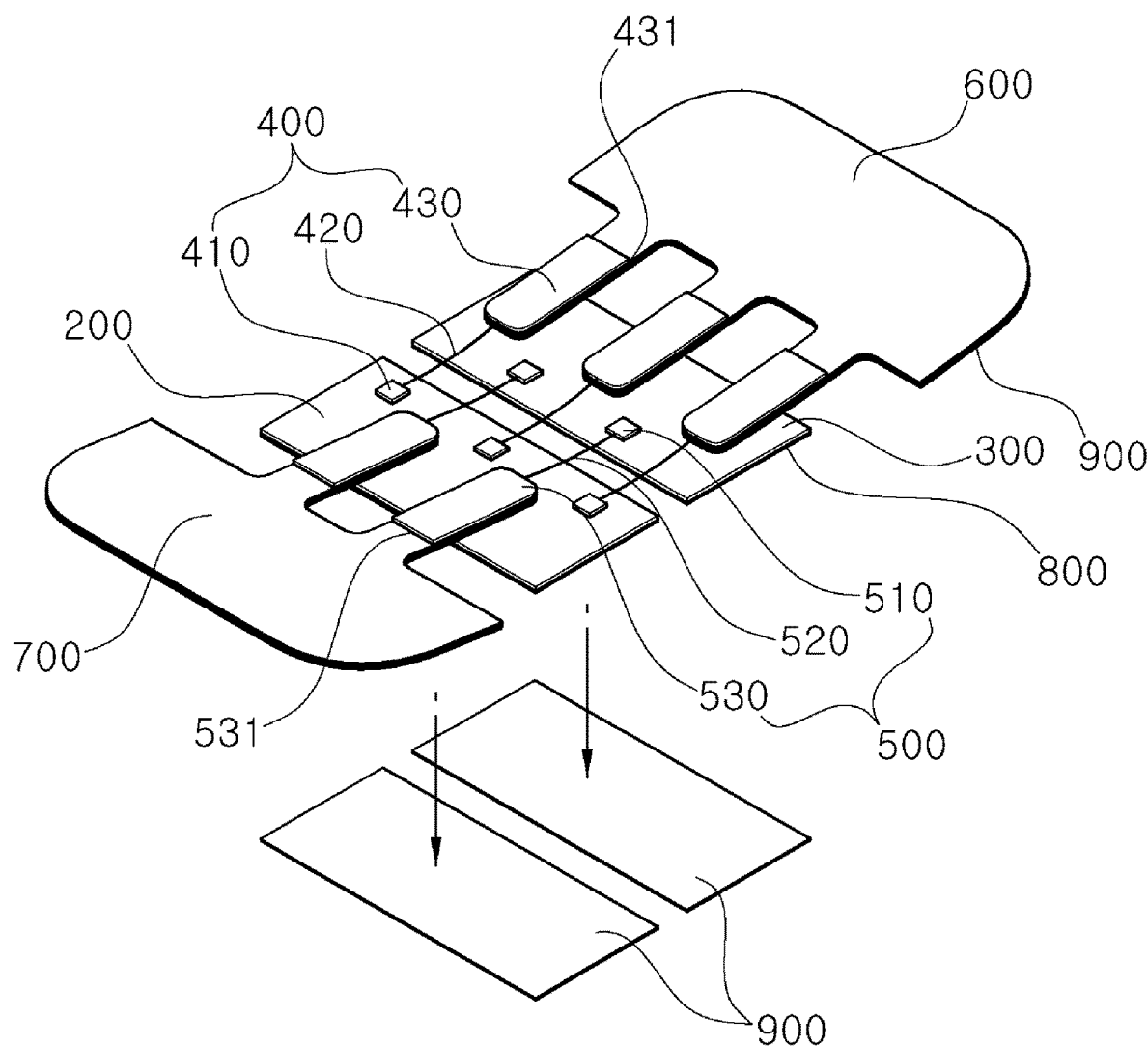
FIGS. 14 to 20 are use state diagrams of the medical skin suturing device according to the first embodiment of the present invention.
Figure 15:
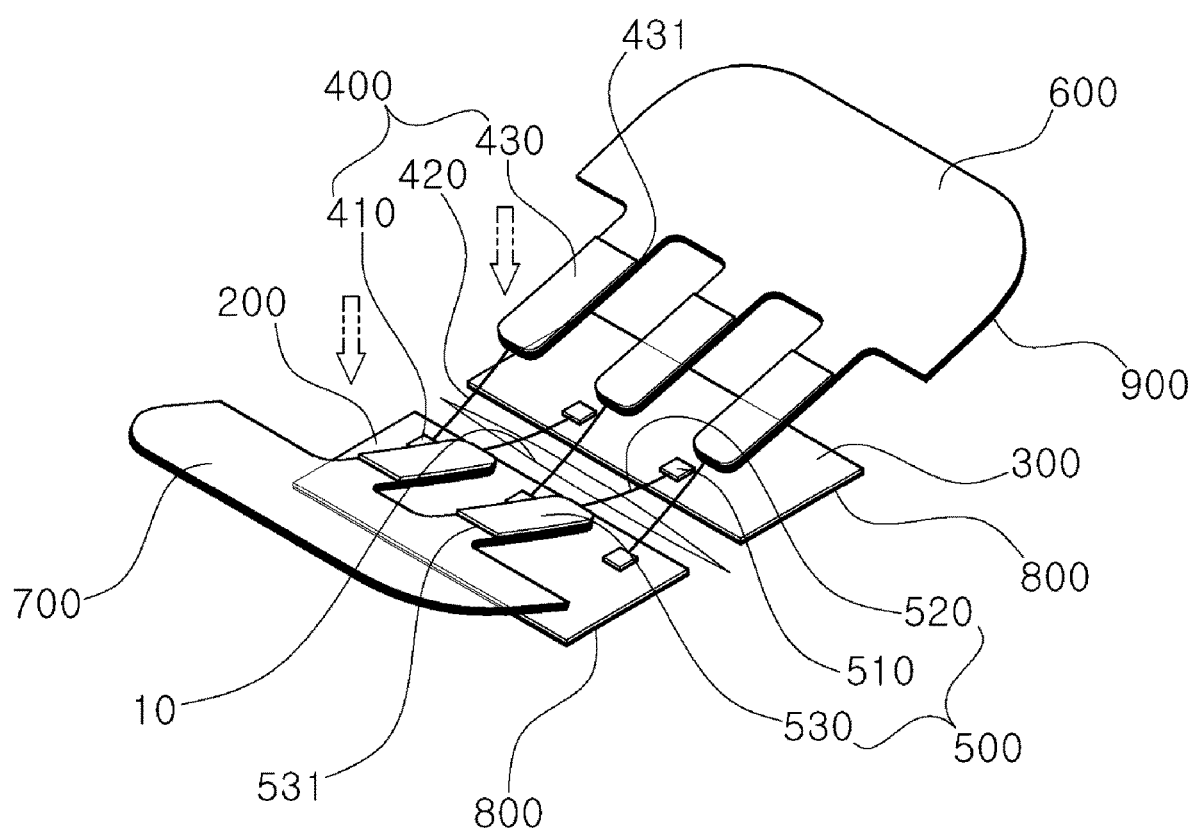

First, as shown in FIG. 14, the protective sheets 900 of the first and second adhesive sheets 200 and 300 are removed, and as shown in FIG. 15, the first and second adhesive sheets 200 and 300 are attached to skins on both sides on the basis of the suture.

Figure 16:
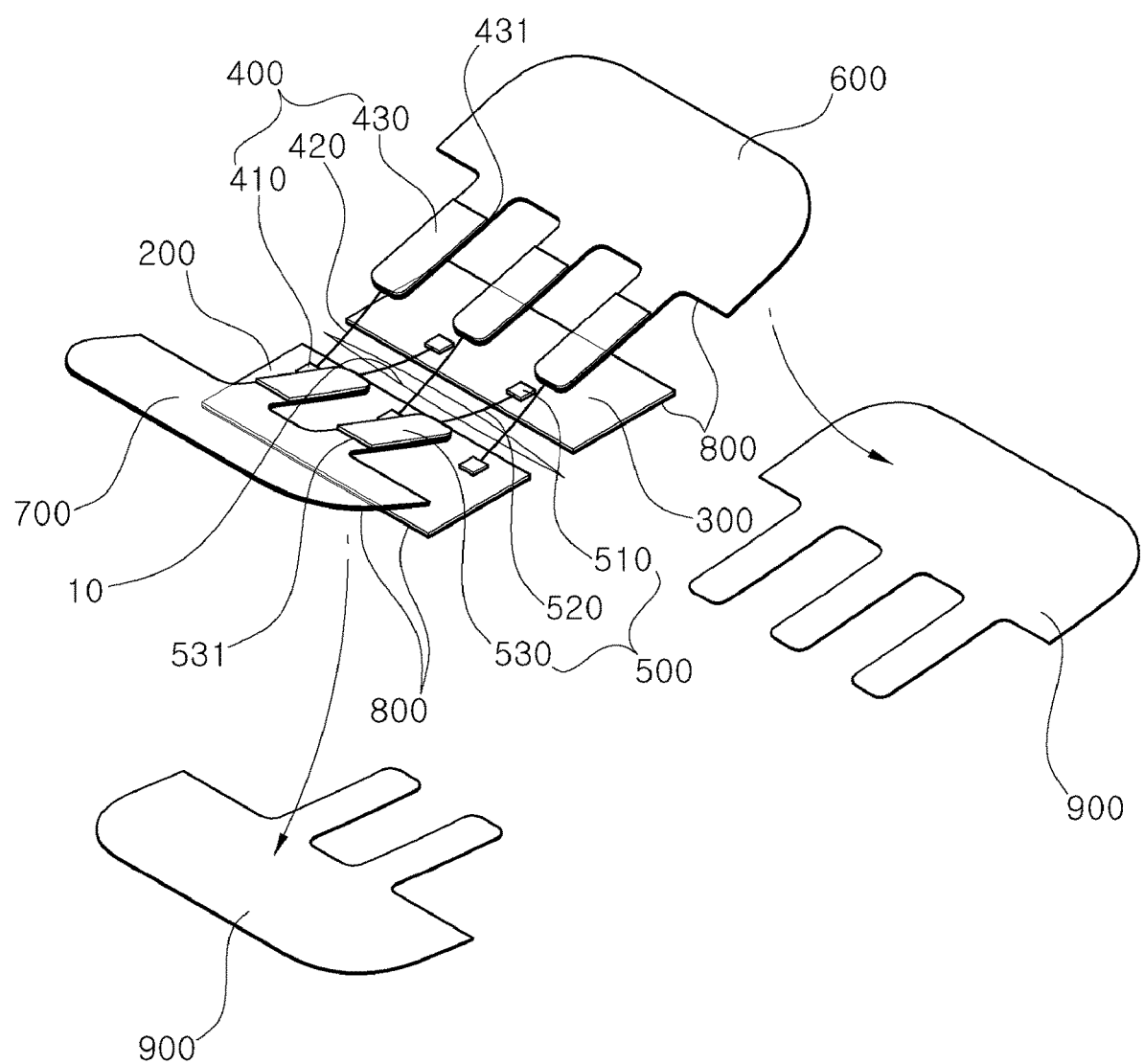

Next, as shown in FIG. 16, the protective sheets 900 are removed from the first handle 600 and the first-second fixing portion 430 and from the second handle 700 and the second-second fixing portion 530. In the embodiment shown in FIG. 16, an example is shown in which the same protective sheets 900 are attached to the first handle 600 and the first-second fixing portion 430, and to the second handle 700 and the second-second fixing portion 530 and each protective sheet 900 is removed at a time. Alternatively, when separate protective sheets 900 are attached to the first-second fixing portion 430, the second-second fixing portion 530, the first handle 600, and the second handle 700, respectively, each of the protective sheets 900 is to be removed separately.

Figure 17:
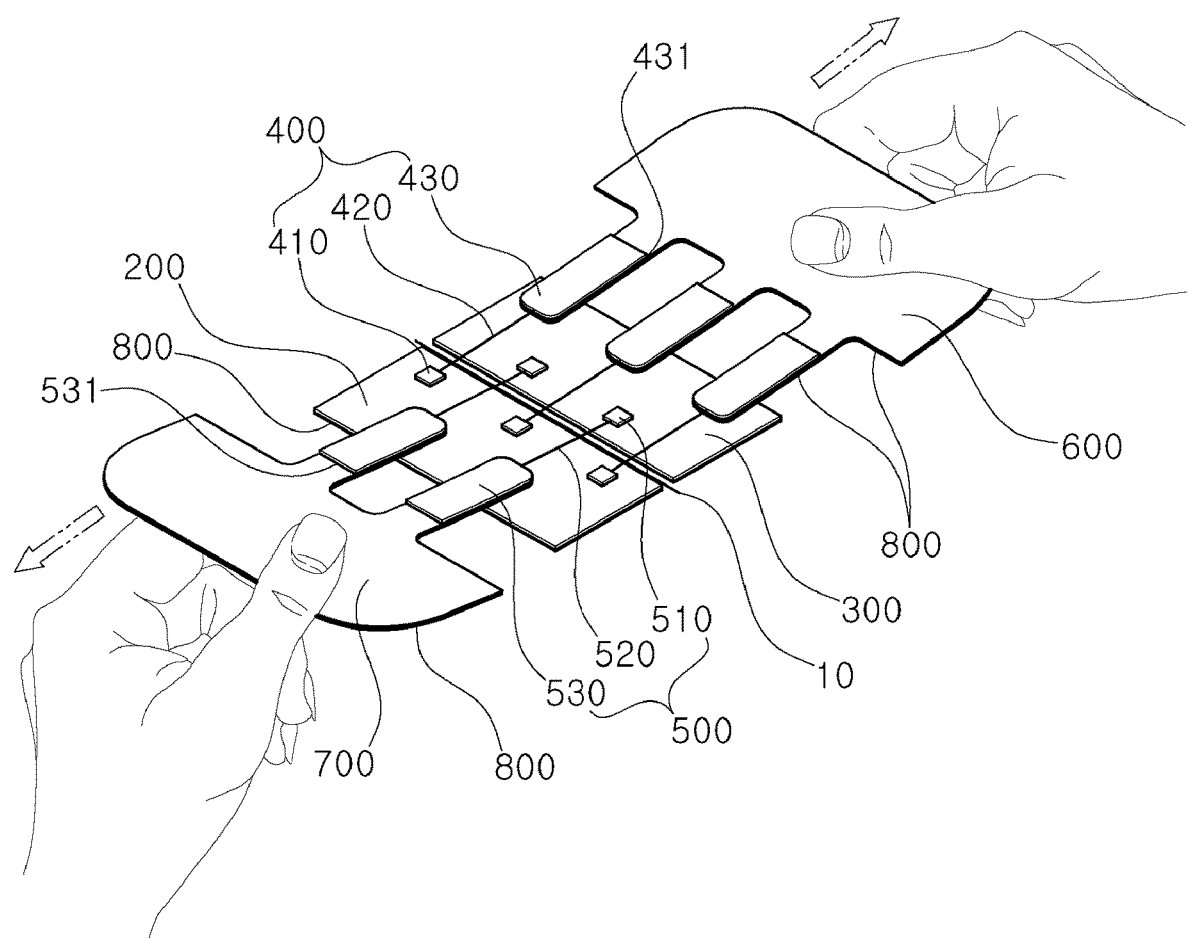

Next, as shown in FIG. 17, the first handle 600 is pulled out of the second adhesive sheet 300 and the second handle 700 is pulled out of the first adhesive sheet 200.

In this process, the first handle 600 pulls the first-second fixing portion 430, the first-second fixing portion 430 pulls the first linear member 420, and the first adhesive sheet 200 to which one end of the first linear member 420 is fixed moves in the direction toward the second adhesive sheet 300. In addition, the second handle 700 pulls the second-second fixing portion 530, the second-second fixing portion 530 pulls the second linear member 520, and the second adhesive sheet 300 to which one end of the second linear member 520 is fixed moves in the direction toward the first adhesive sheet 200. In this case, the skins on both sides of the suture to which the first adhesive sheet 200 and the second adhesive sheet 300 are respectively attached get closed to each other while narrowing the gap, and then are sutured.

Figure 18:
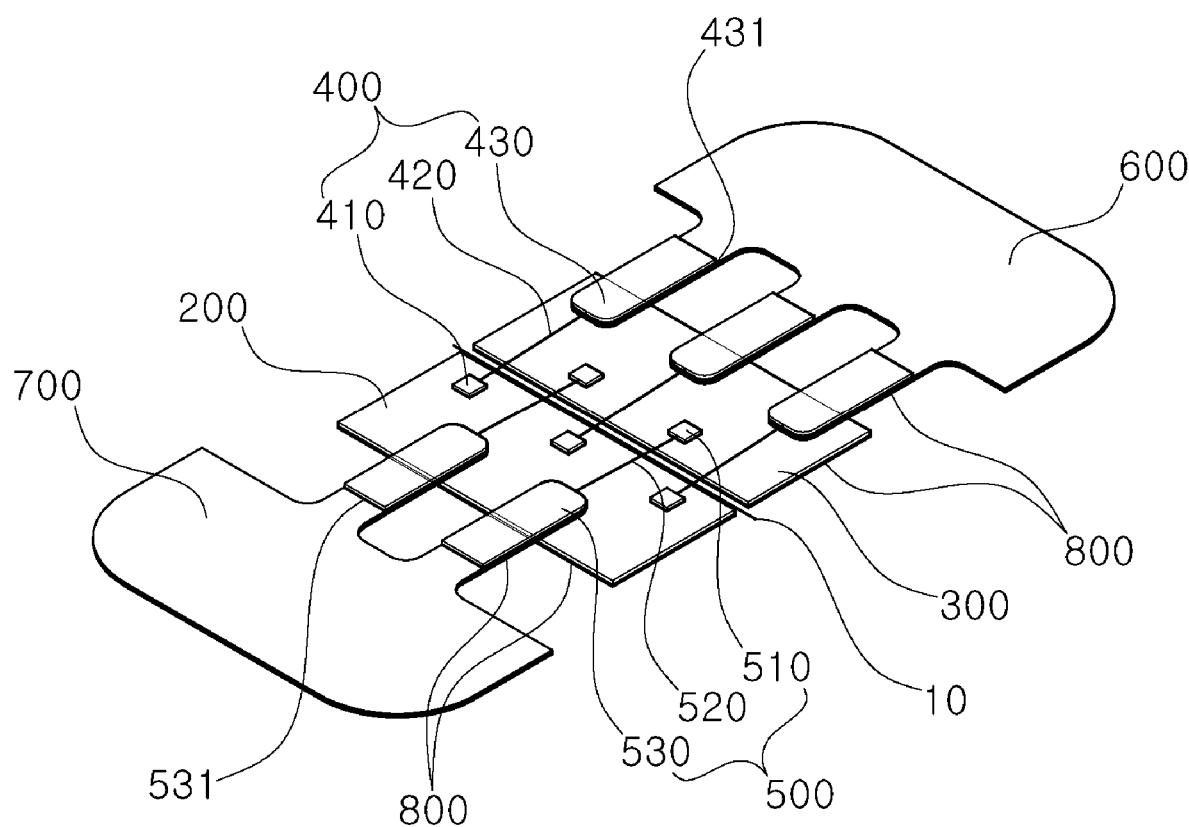

Then, as shown in FIG. 18, the first handle 600 and the second handle 700 are attached to the skin in the state where the suture is sutured. At the same time, the first-second fixing portion 430 is attached to the second adhesive sheet 300 and the skin, and the second-second fixing portion 530 is attached to the first adhesive sheet 200 and the skin.

In this case, the first-second fixing portion 430 and the first handle 600, and the second-second fixing portion 530 and the second handle 700 support the tension applied to the first and second linear members 520 by the force that the suture is going to open again.

Figure 19:
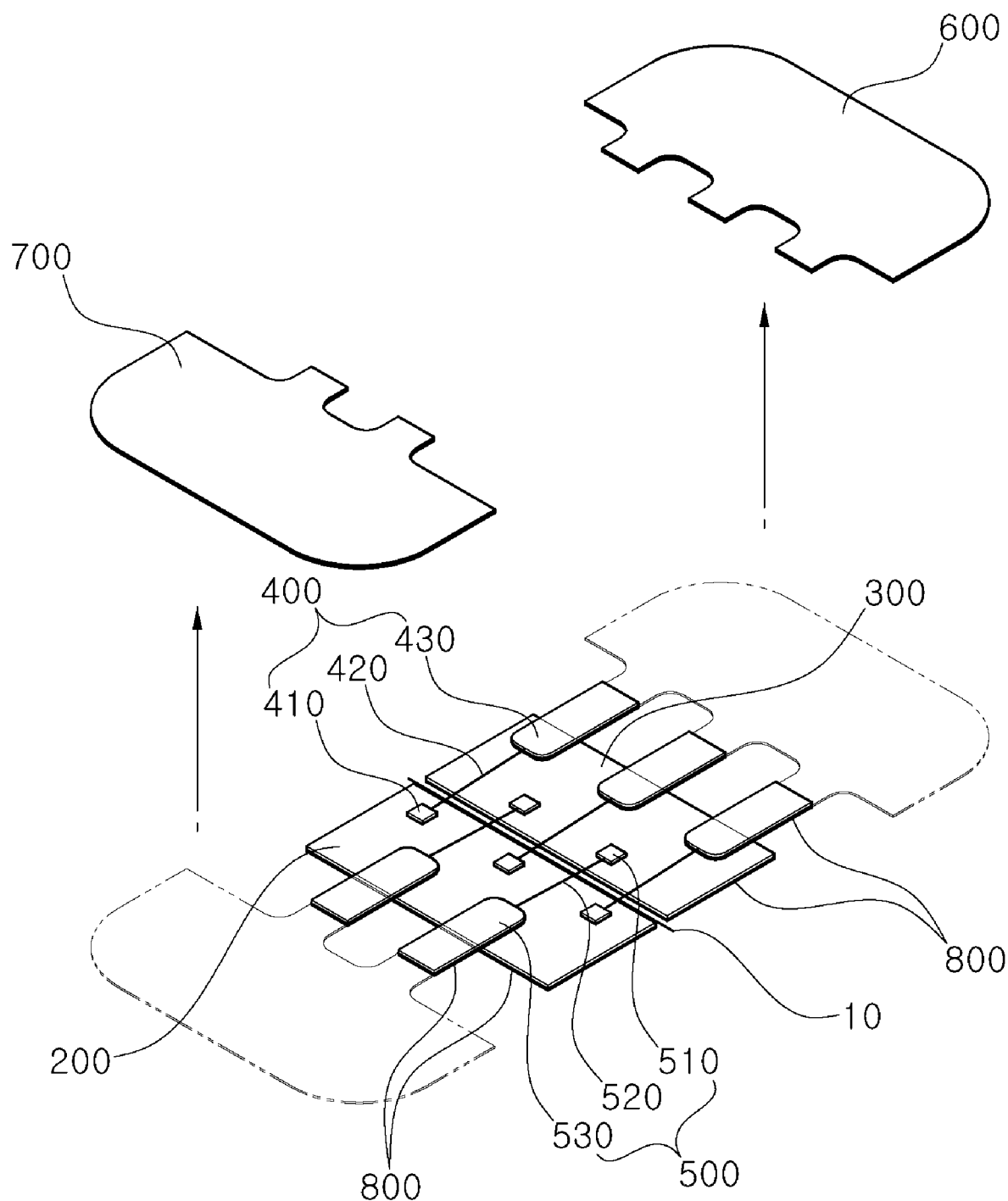
Figure 20:
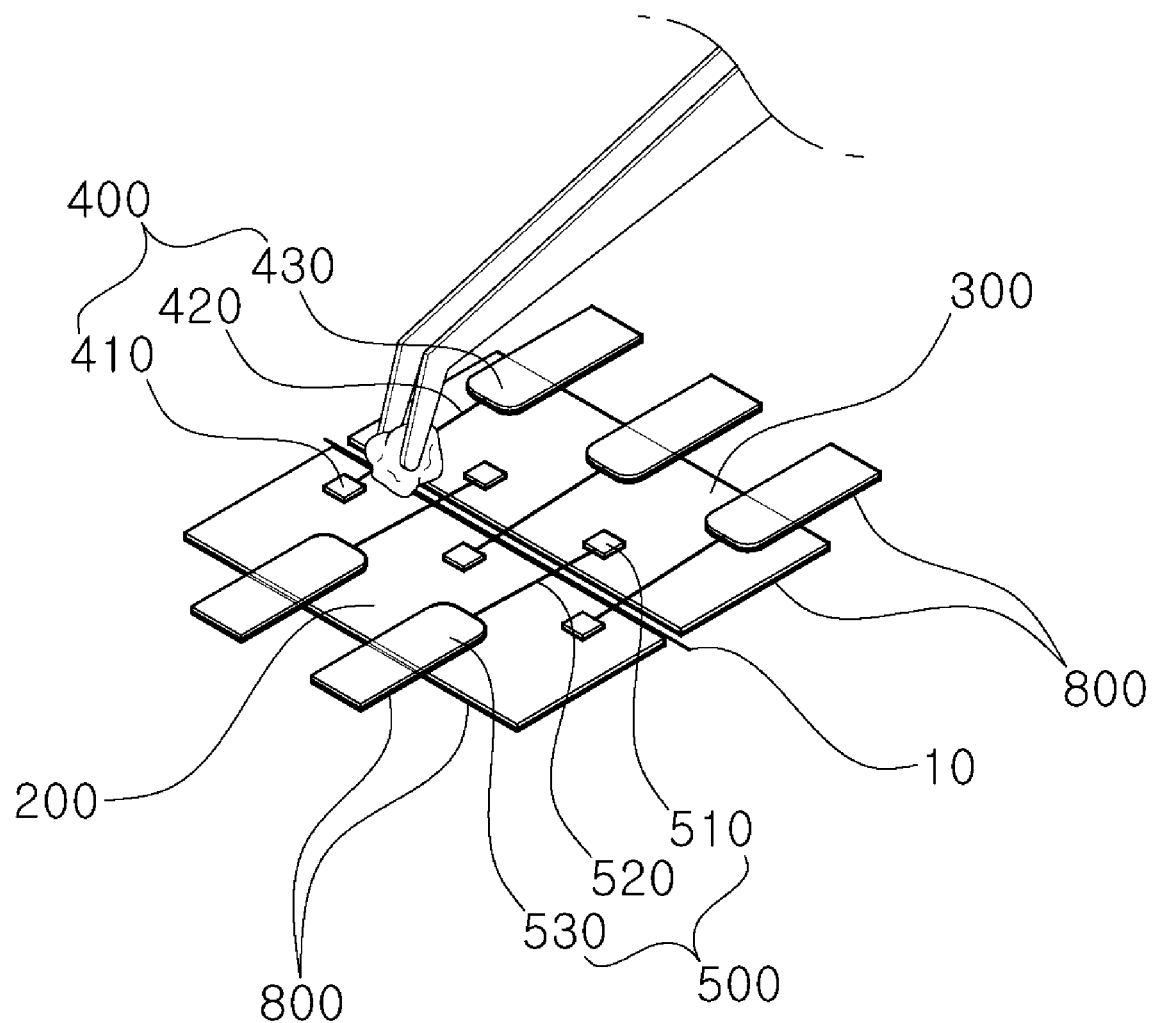

As shown in FIG. 19, the first and second handles 600 and 700 may be removed by cutting as needed, and for this purpose, cut lines 431 and 531 may be formed on the first-second fixing portion 430 and the second-second fixing portion 530.

With the medical skin suturing device 100 according to the first embodiment of the present invention, as the first and second linear members 420 and 520 are made of a thin thread or a string of a synthetic resin material, a significant portion of the suture is exposed between the first linear member 420 and the second linear member 520. Therefore, even after the procedure by the medical skin suturing device 100, a follow-up treatment such as disinfection for the suture is made easy as shown in FIG. 10.

Third Embodiment

Figure 21:
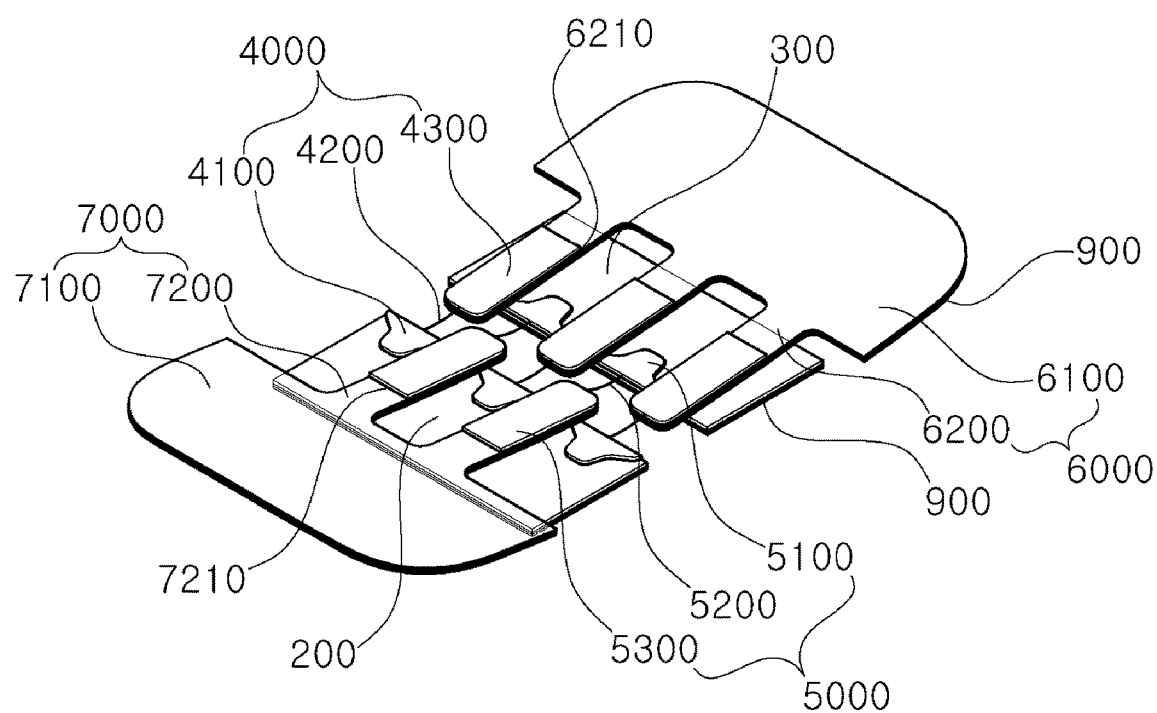
FIG. 21 is a perspective view showing a medical skin suturing device according to a second embodiment of the present invention.
Figure 22:
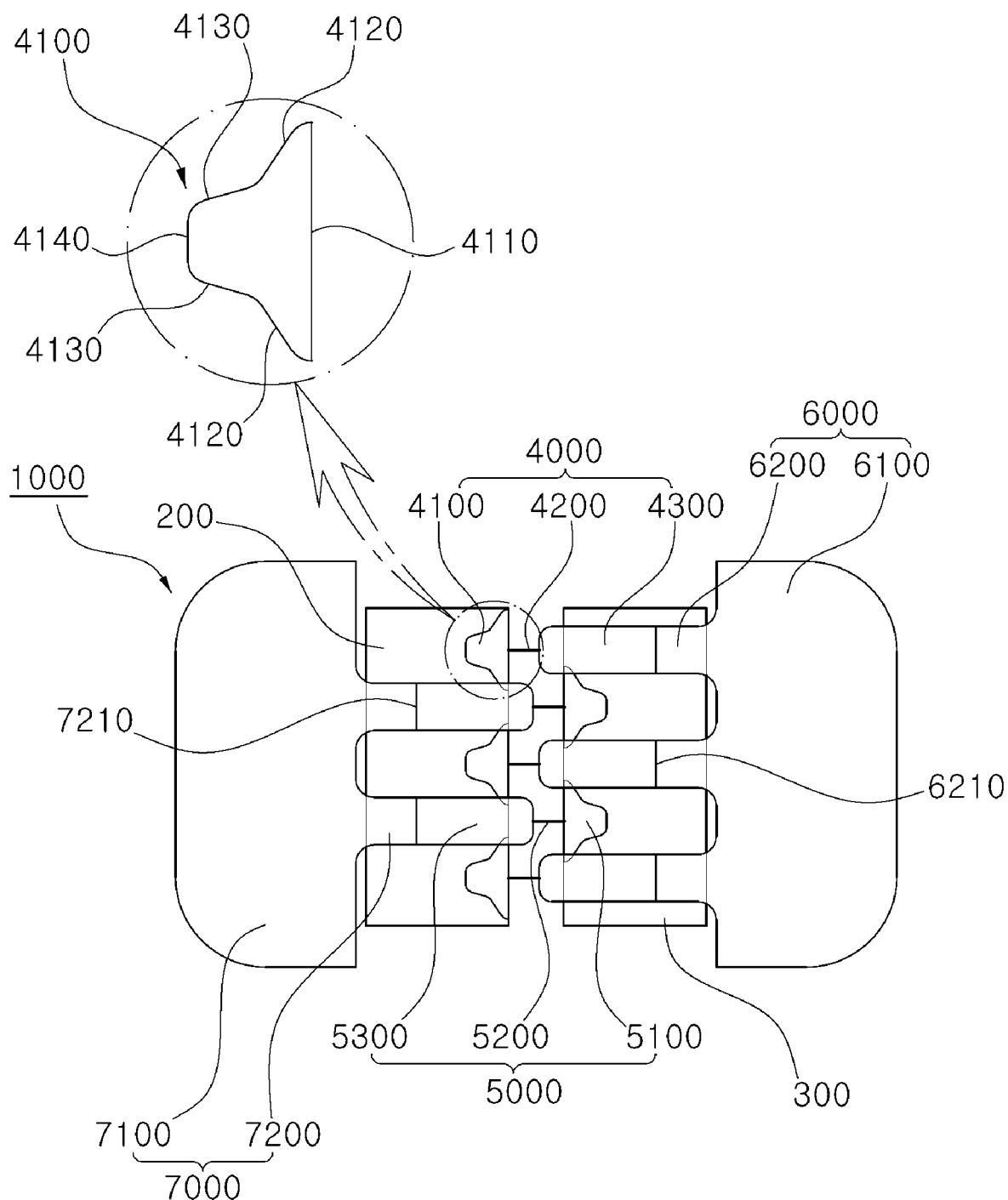
FIG. 22 is a plan view showing the medical skin suturing device according to the second embodiment of the present invention.

FIG. 21 is a perspective view showing a medical skin suturing device according to a second embodiment of the present invention, and FIG. 22 is a plan view showing the medical skin suturing device according to the second embodiment of the present invention.

A medical skin suturing device 1000 according to the second embodiment of the present invention is similar in overall configuration to the first embodiment described above in that a first adhesive sheet 200 and a second adhesive sheet 300 are adhered to the skins on both sides of the suture, respectively, and the first and second adhesive sheets 200 and 300 are pulled in the direction in contact with each other to close the suture.

However, there is a difference in the configuration of first and second traction members 4000 and 5000 and first and second handles 6000 and 7000 compared to the above-described first embodiment, and the medical skin suturing device 1000 according to the second embodiment of the present invention will be described in detail with respect to with a focus on the difference from the first embodiment described above.

The first adhesive sheet 200 and the second adhesive sheet 300 are the same as those of the first embodiment described above, and therefore, the same reference numerals are given and descriptions thereof will not be repeated below.

The first traction member 4000 has one end attached to the first adhesive sheet 200 and the other end extending over the second adhesive sheet 300, and the second traction member 5000 has one end attached to the second adhesive sheet 300 and the other end extending over the first adhesive sheet 200. In addition, as in the first embodiment described above, a plurality of first and second traction members 4000 and 5000 are alternately formed in a zigzag form along the length direction of the first and second adhesive sheets 200 and 300. For example, the first traction member 4000 and the second traction member 5000 may be alternately arranged one by one along the suture. In this case, it is desirable to dispose the first and second traction members 4000 and 5000 in different numbers from each other such that the traction force by the first and second traction members 4000 and 5000 is uniformly applied to the first and second adhesive sheets 200 and 300.

The first traction member 4000 includes a first-first fixing portion 4100 attached to the first adhesive sheet 200, a first linear member 4200 formed to extend from the first-first fixing portion 4100 toward the second adhesive sheet 300, and a first-second fixing portion 4300 formed at the end of the first linear member 4200 and attached to the first handle 6000.

The second traction member 5000 includes a second-first fixing portion 5100 attached to the second adhesive sheet 300, a second linear member 5200 formed to extend from the second-first fixing portion 5100 toward the first adhesive sheet 200, and a second-second fixing portion 5300 formed at the end of the second linear member 5200 and attached to the second handle 7000.

Here, since the first-first fixing portion 4100 and the second-first fixing portion 5100, the first linear member 4200 and the second linear member 5200, and the first-second fixing portion 4300 and the second-second fixing portion 5300 have the same configurations in pairs, configurations of the first and second traction members 4000 and 5000 according to the second embodiment will be described in detail as an example of the first traction member 4000 below.

According to the second embodiment of the present invention, the first-first fixing portion 4100, the first linear member 4200, and the first-second fixing portion 4300 are integrally formed of the same synthetic resin material such as nylon, for example.

The first-first fixing portion 4100 is attached to the upper surface of the first adhesive sheet 200 by a medical adhesive. In this case, the first-first fixing portion 4100 may be formed in various forms such as a circle or an oval, or a polygon such as a triangle or a square. However, this is merely an embodiment of the present invention, and the specific form of the first-first fixing portion 4100 may be appropriately selected as needed.

It is desirable that the first-first fixing portion 4100 is formed in a trumpet shape or a trapezoidal shape in which a width is extended toward the suture opposing edge inside the first adhesive sheet 200. More specifically, the borders of the first-first fixing portion 4100 include a first straight portion 4110 extending along an inner edge of the first adhesive sheet 200, a pair of first inclined portions 4120 inclined inward of the first adhesive sheet 200 to face each other at both ends of the first straight portion 4110, a pair of second inclined portions 4130 respectively extending at an angle greater than the inclined angle of the first inclined portion 4120 at the ends of the pair of first inclined portions 4120, and a second straight portion 4140 connecting the ends of the pair of second inclined portions 4130.

As described above, the reason why the first-first fixing portion 4100 is formed to have the outer width larger than the inner width is that uniform force is applied along the suture opposing edges of the first adhesive sheet 200 as a whole by dispersing the force transmitted to the first-first fixing portion 4100 when the first-first fixing portion 4100 is pulled by the first linear member 4200. Therefore, it is desirable that the first-first fixing portion 4100 is attached such that the first straight portion 4110 is adjacent to the suture opposing edge of the first adhesive sheet 200. The first linear member 4200 is a member extending on one side of the first-first fixing portion 4100. The first linear member 4200 may have a wire shape having a small width (or diameter or thickness) compared to a length, and may be, for example, a string, strap, or tube of a synthetic resin material.

The first-second fixing portion 4300 applies a traction force to the first linear member 4200 while supporting the tension applied to the first linear member 4200, and is integrally formed with the first linear member 4200 at the end of the first liner member 4200. As an example, the first-second fixing portion 4300 may be formed in a rectangular shape corresponding to the shape of a first support 6200 of the first handle 6000 to be described later, as shown in the figure. However, this is merely an embodiment of the present invention, and the specification and shape of the first-second fixing portion 4300 may be appropriately selected as needed as far as it is attached to the first support 6200 of the first handle 6000 to support the tension applied to the first linear member 4200.

The first handle 6000 and the second handle 7000 serve as handles for pulling the first traction member 4000 and the second traction member 5000, respectively, and the first handle 6000 is formed above the second adhesive sheet 300 and the second handle 7000 is formed above the first adhesive sheet 200.

Here, the first handle 6000 includes a first gripping portion 6100 and the first support 6200 protruding from the inner edge of the first gripping portion 6100 toward the suture, where a plurality of the first supports 6200 is integrally formed with the first gripping portion 6100 while being spaced apart from each other at predetermined intervals along the inner edge of the first gripping portion 6100.

In addition, the second handle 7000 includes a second gripping portion 7100 and a second support 7200 protruding from the inner edge of the second gripping portion 7100 toward the suture, where a plurality of the second supports 7200 are integrally formed with the second gripping portion 7100 while being spaced apart from each other at predetermined intervals along the inner edge of the gripping portion 7100.

Here, the first gripping portion 6100 and the second gripping portion 7100, and the first support 6200 and the second support 7200 have the same configurations in pairs, and thus configurations of the first and second handles 6000 and 7000 according to the second embodiment of the present invention will be described in detail below.

The first-second fixing portion 4300 of the above-mentioned first traction member 4000 is attached to the upper side of the first support 6200 by a medical adhesive. Meanwhile, the first handle 6000 including the first support 6200 and the first gripping portion 6100 may be, for example, a hydrocolloid band used as a medical wet band, and the lower surface of the first handle 6000 is provided with the adhesive layer 800 and the protective sheet 900.

FIGS. 23 to 28 are use state diagrams of the medical skin suturing device according to the second embodiment of the present invention, and a method of using a medical skin suturing device according to the second embodiment of the present invention will be described in detail below with reference to the drawings.

Figure 23:
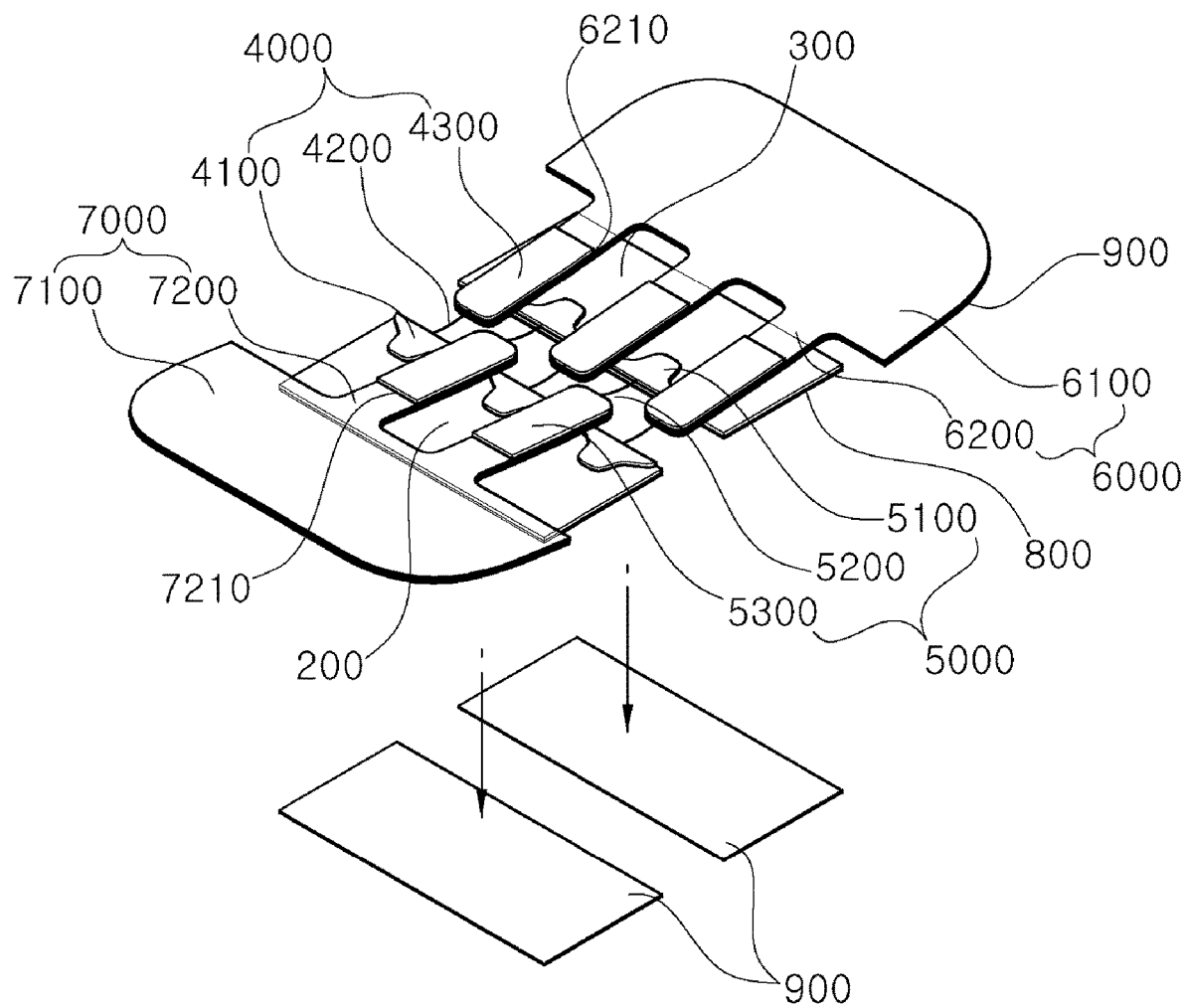
FIGS. 23 to 28 are use state diagrams of the medical skin suturing device according to the second embodiment of the present invention.
Figure 24:
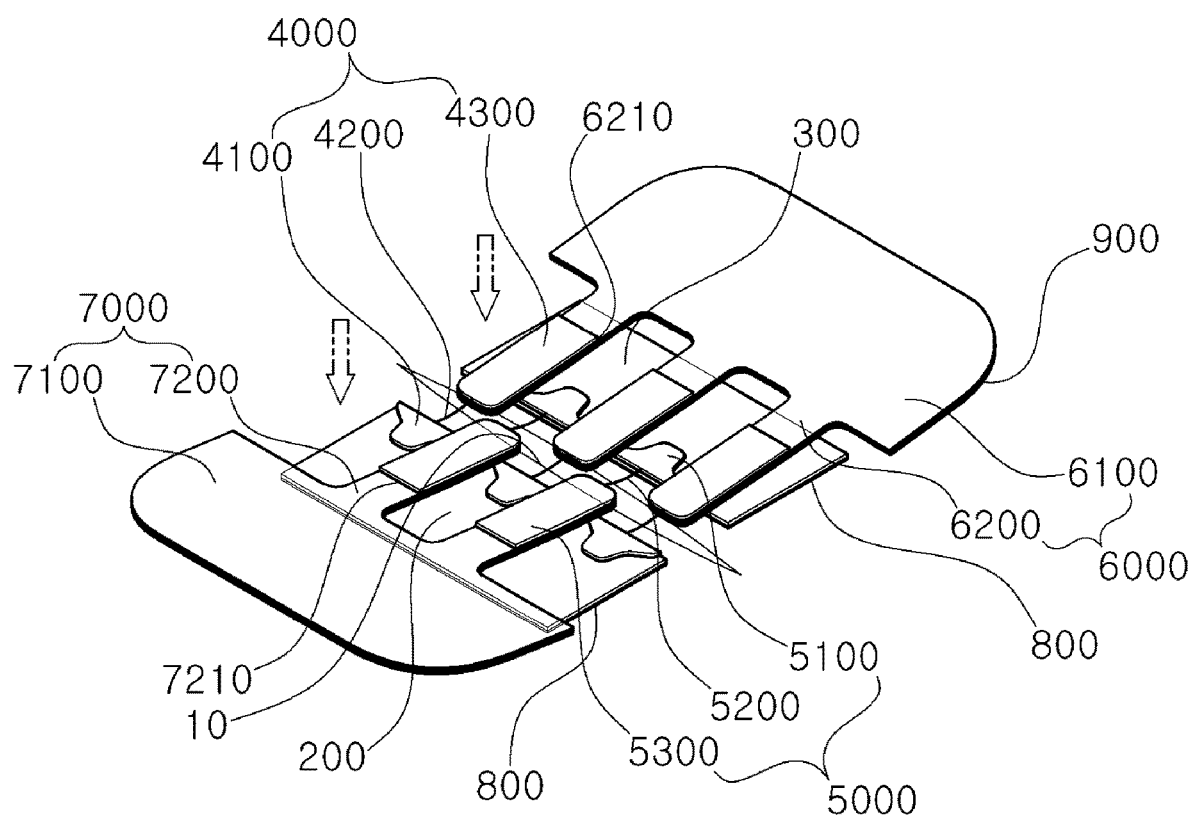

First, as shown in FIG. 23, the protective sheets 900 of the first and second adhesive sheets 200 and 300 are removed, and as shown in FIG. 14, the first and second adhesive sheets 200 and 300 are attached to skins on both sides on the basis of the suture.

Figure 25:
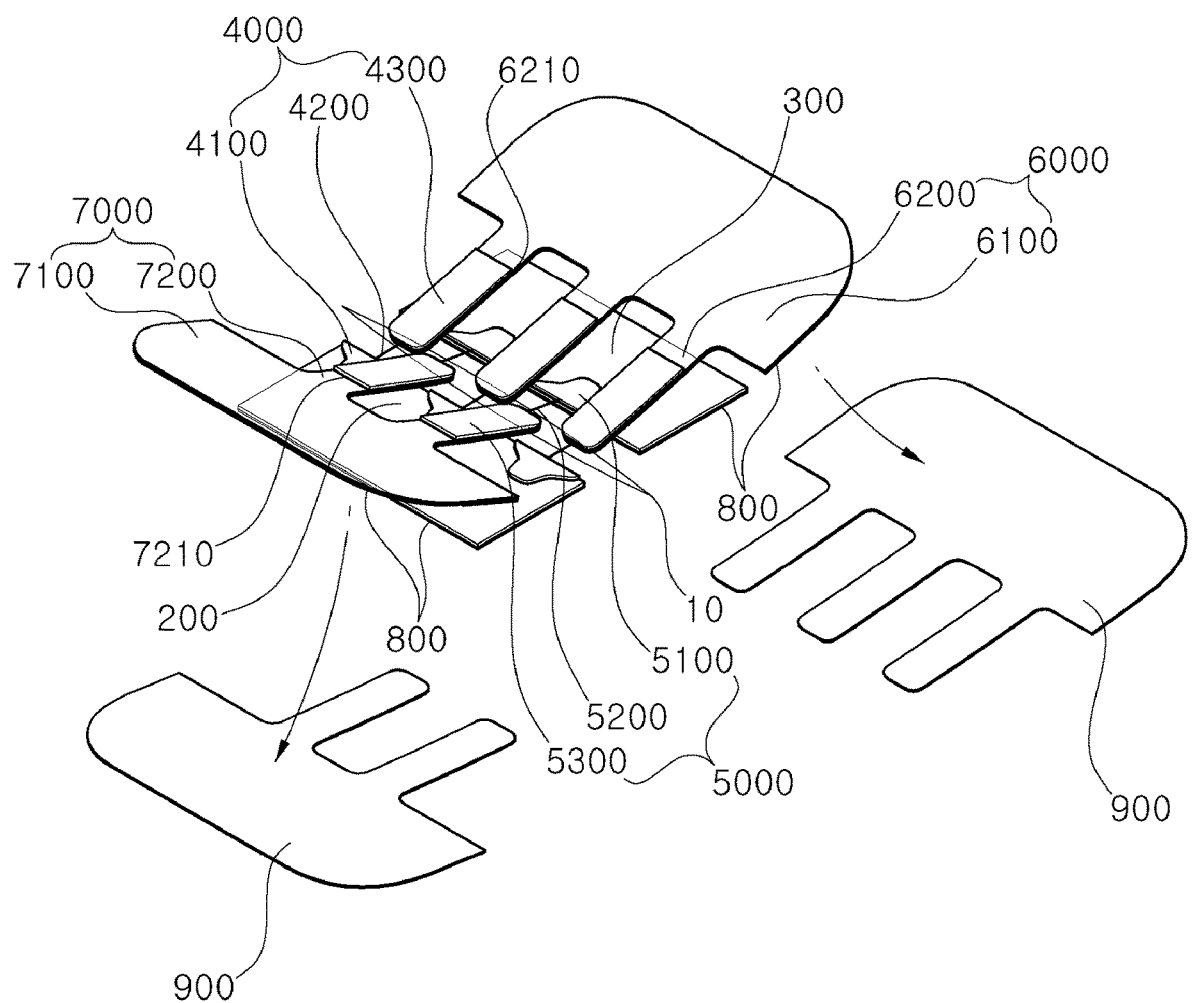
Figure 26:
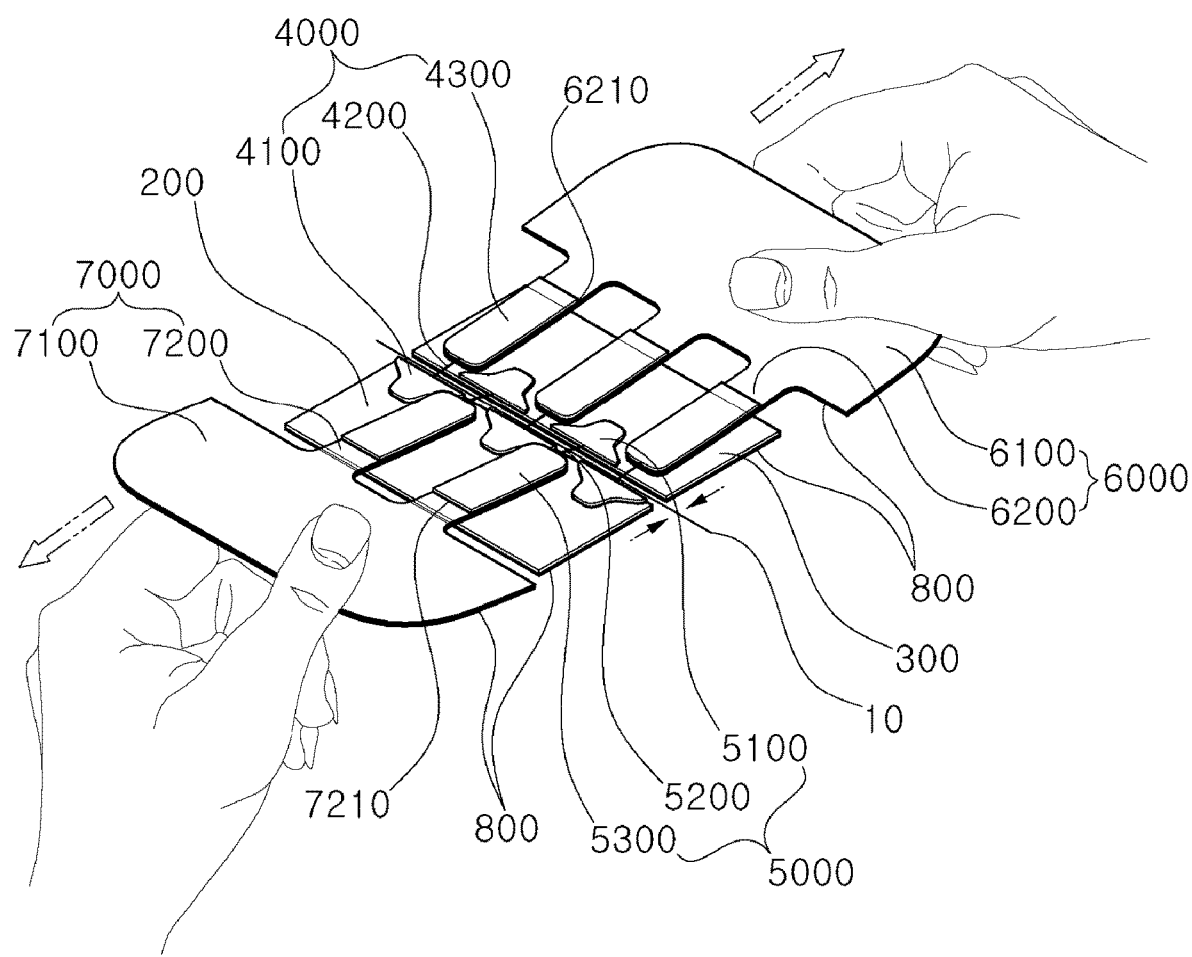

Next, the protective sheets 900 are removed from the first handle 6000 and the second handle 7000 as shown in FIG. 25, and the first gripping portion 6100 is pulled out of the adhesive sheet 300 and the second gripping portion 7100 is pulled out of the first adhesive sheet 200, as shown in FIG. 26.

In this case, the first support 6200 pulls the first-second fixing portion 4300, the first-second fixing portion 4300 pulls the first-first fixing portion 4100 through the first linear member 4200, and the first adhesive sheet 300 to which the first-first fixing portion 4100 is attached moves in the direction toward the second adhesive sheet 300.

In addition, the second support 7200 pulls the second-second fixing portion 5300, the second-second fixing portion 5300 pulls the second-first fixing portion 5100 through the second linear member, and the second adhesive sheet 300 to which the second-first fixing portion 5100 is attached moves in the direction toward the first adhesive sheet 200.

That is, by pulling the first handle 6000 and the second handle 7000 in opposite directions, the skins on both sides of the suture to which the first adhesive sheet 200 and the second adhesive sheet 300 are attached, respectively, get closed while narrowing the gap and then are brought into contact with each other and are sutured.

Figure 27:
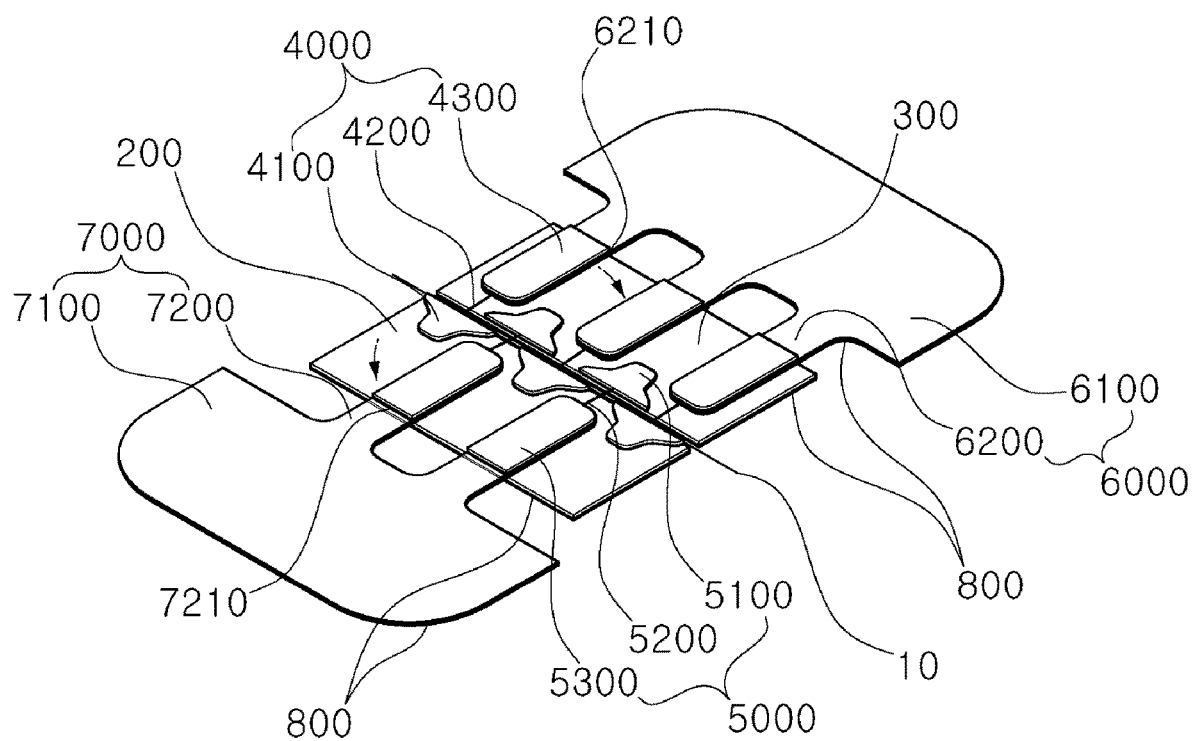
Figure 28:
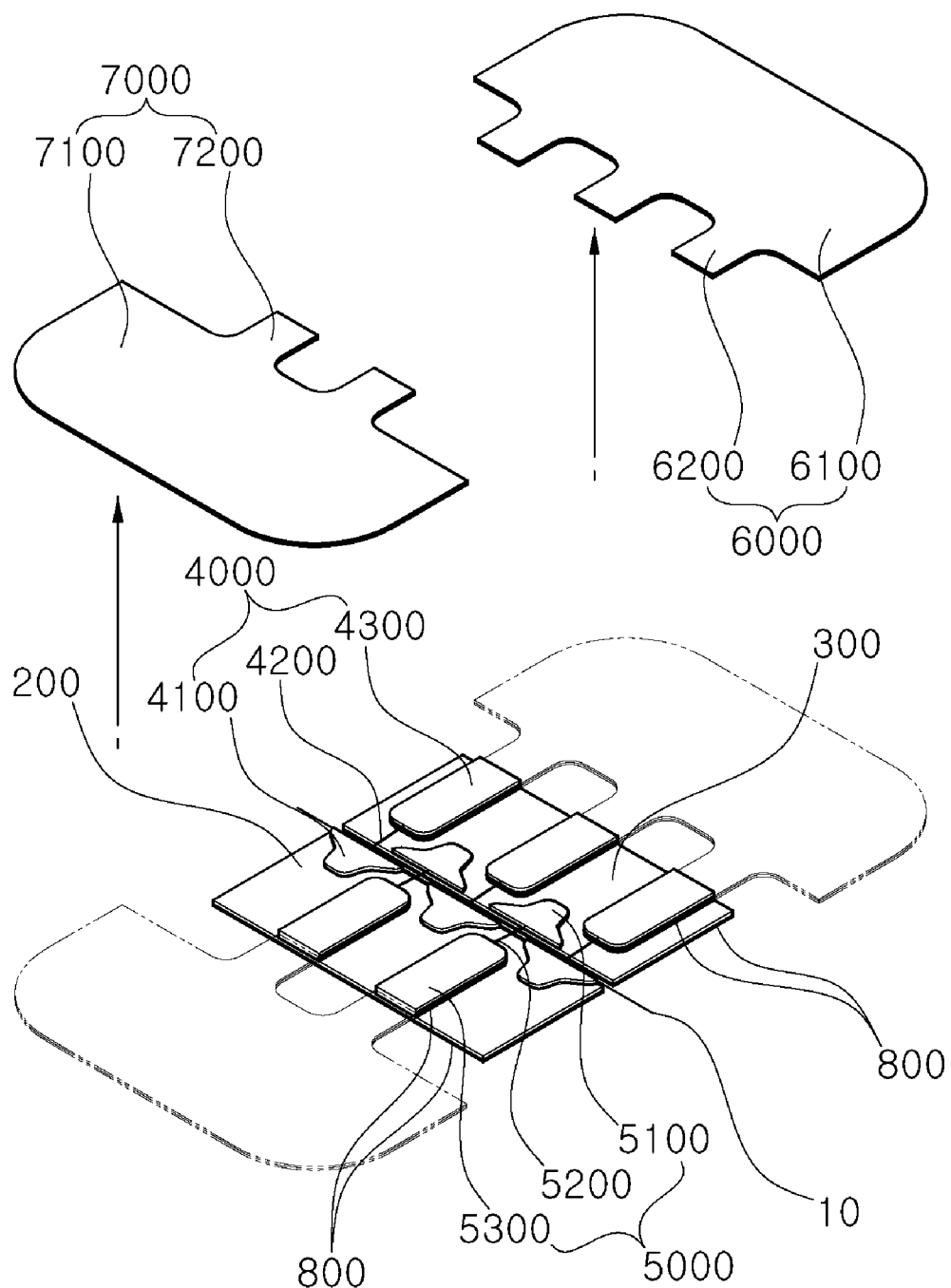

Then, as shown in FIG. 27, the first gripping portion 6100 and the second gripping portion 7100 are attached to the skin in the state where the suture is sutured. In this case, the first support 6200 is attached to the second adhesive sheet 300 and the second support 7200 is attached to the first adhesive sheet 200 to support the tension force applied to the first linear member 4200 and the second linear member 5200.

Of course, depending on the degree of pulling the first and second handles 7000, the first and second supports 6200 and 7200 may be attached to the skin past the borders of the second and first adhesive sheets 300 and 200. However, it is desirable that the first-second fixing portion 4300 does not protrude outside the second adhesive sheet 300 and the second-second fixing portion 5300 does not protrude outside the first adhesive sheet 200. The reason is for preventing the ends of the first-second fixing portion 4300 and the second-second fixing portion 5300 from being separated by being caught by an external object such as clothing, or preventing the adhesive force from being weakened.

The first and second gripping portions 6100 and 7100 may be cut out and removed, or the first and second gripping portions 6100 and 7100 may be cut out and removed together with some of the first and second supports 6200 and 7200 protruding outside the first and second adhesive sheets 200 and 300 as shown in FIG. 18, as needed, and for this purpose, cut lines 6210 and 7210 may be formed on the first and second supports 6200 and 7200, respectively.

With the medical skin suturing device 1000 according to the second embodiment of the present invention, as the first and second linear members 4200 and 5200 are made of a synthetic resin material and are thin threads, straps or strings, a significant portion of the suture is exposed between the first linear member 4200 and the second linear member 5200. Therefore, even after the procedure by the medical skin suturing device 1000, a follow-up treatment such as disinfection for the suture is made easy.

In addition, since the first-first fixing portion 4100 and the second-first fixing portion 5100 are formed to have larger outer widths than the inner widths, the forces transmitted from the first and second linear members 4200 and 5200 may each disperse, and thus uniform forces may be applied along the suture opposing edges of the first and second adhesive sheets 200 and 300.

Fourth Embodiment

Figure 29:
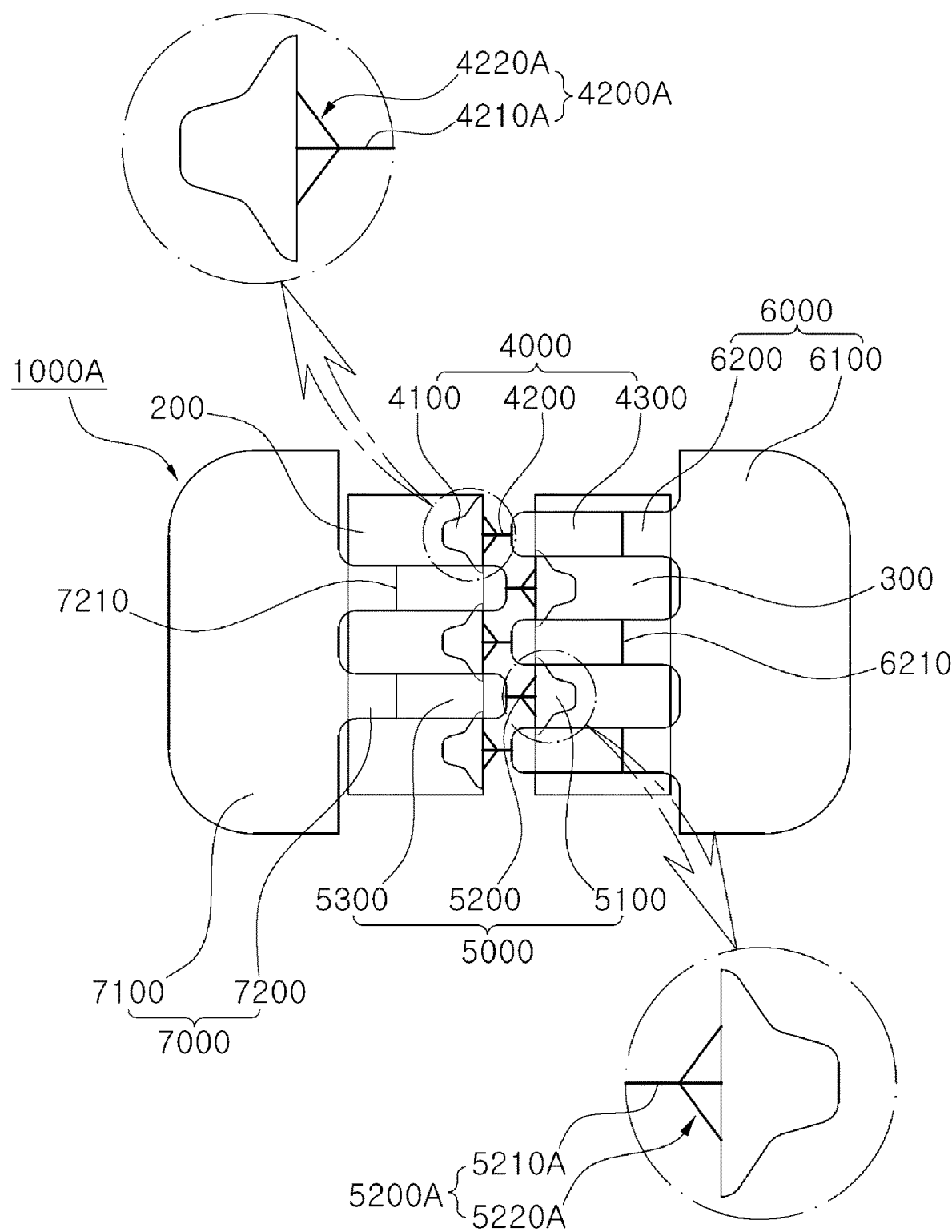
FIG. 29 is a partially enlarged view showing a first linear member according to a third embodiment of the present invention.

FIG. 29 is a partially enlarged view showing a first linear member according to a third embodiment of the present invention.

A medical skin suturing device 1000A according to the third embodiment of the present invention has a similar overall structure to the medical skin suturing device 1000 of the second embodiment described above, except that first and second linear members 4200A and 5200A are different in that one end of each thereof is branched into a plurality and extends to the first-first and second-first fixing portions 4100 and 5100.

Therefore, the same reference numerals will be given to the same configuration as the second embodiment described above and the description thereof will not be repeated. Hereinafter, the third embodiment of the present invention will be described with reference to FIG. 29.

The first linear member 4200A according to the third embodiment of the present invention includes a first body part 4210A, one end of which extends to a first-second fixing portion 4300, and a plurality of first branch portions 4220A branched from the other end of the first body part 4210A and extending to the first-first fixing portion 4100.

Similarly, the second linear member 5200A includes a second body part 5210A, one end of which extends to a second-second fixing portion 5300, and a plurality of second branch portions 5220A branched from the other end of the second body part 5210A and extending to the second-first fixing portion 5100.

As described above, when one end of each of the first and second linear members 4200A and 5200A is branched into a plurality and extends to the first-first and second-first fixing portions 4100 and 5100, the traction force by the first and second linear members 4200A and 5200A is uniformly applied to the first-first and second-first fixing portions 4100 and 5100 as a whole, which may be effective in preventing deformation due to local concentration of force such as separation of the first-first and second-first fixing portions 4100 and 5100, distortion of the first and second adhesive sheets 200 and 300, or the like.

Although the embodiments of the present invention have been described above, it is understood that those skilled in the art to which the present invention pertains can make various modifications without departing from the claims of the present invention.

REFERENCE SIGNS LIST

Band for surgical wound suture 1
Band 10
First band 10-1
First left band 10-11
First right band 10-12
Second band 10-2
Second left band 10-21
Second right band 10-22
Support layer 11
Adhesive layer 12
Release paper layer 13
Extension portion 13-1
Inner release paper 13-2
Outer release paper 13-3
Connecting portion 20
Band attachment means 21
Incision 101
100,1000,1000A: Medical skin suturing device
200: First adhesive sheet
300: Second adhesive sheet
400,4000: First traction member
420,4200,4200A: First linear member
500,5000: Second traction member
520,5200,5200A: Second linear member
600,6000: First handle
700,7000: Second handle

INDUSTRIAL APPLICABILITY

The object of the present invention is to provide a band for surgical wound suture.

The invention claimed is:
1. A band for surgical wound suture, comprising:
a first adhesive sheet and a second adhesive sheet that are configured to be adhered to a skin on both sides of the surgical wound suture;
a plurality of first traction members, each having one end attached to the first adhesive sheet and another end extending over the second adhesive sheet;
a plurality of second traction members, each having one end attached to the second adhesive sheet and another end extending over the first adhesive sheet;
a first handle disposed above the second adhesive sheet and coupled with the another end of each of the plurality of first traction members;
a second handle disposed above the first adhesive sheet and coupled with the another end of each of the plurality of second traction members,
wherein the plurality of first traction members and the plurality of second traction members are alternately arranged in a zigzag form along a length direction of the first and second adhesive sheets,
wherein each of the first handle and the second handle includes a gripping portion and a plurality of supports protruding from an inner edge of the gripping portion toward the surgical wound suture, wherein the plurality of supports of the first and second handles are integrally formed with the respective gripping portion of the first and second handles and spaced apart from each other at predetermined intervals along the inner edge of the respective gripping portion of the first and second handles, wherein each of the plurality of first traction members comprises:
- a first-first fixing portion attached to the first adhesive sheet;
- a first linear member extending from the first-first fixing portion toward the second adhesive sheet; and
- a first-second fixing portion connected to an end of the first linear member and attached to the first handle, wherein the first-first fixing portion has a trumpet shape or a trapezoidal shape in which a width thereof extends toward a suture opposing edge inside the first adhesive sheet, and wherein borders of the first-first fixing portion comprise:
- a first straight portion extending along an inner edge of the first adhesive sheet;
- a pair of first inclined portions inclined inward of the first adhesive sheet to face each other at both ends of the first straight portion;
- a pair of second inclined portions respectively extending at an angle greater than an inclined angle of the pair of first inclined portions at ends of the pair of first inclined portions; and
- a second straight portion connecting ends of the pair of second inclined portions.

2. The band for surgical wound suture of claim 1, wherein each of the plurality of second traction members comprises:
- a second-first fixing portion attached to the second adhesive sheet;
- a second linear member extending from the second-first fixing portion toward the first adhesive sheet; and
- a second-second fixing portion connected to an end of the second linear member and attached to the second handle.

3. The band for surgical wound suture of claim 1, wherein the first-second fixing portion has a rectangular shape corresponding to a shape of a first support of the plurality of supports of the first handle.

4. The band for surgical wound suture of claim 3, wherein the first-second fixing portion is configured to be attached to an upper side of the first support by a medical adhesive.

5. The band for surgical wound suture of claim 1, wherein the first handle has a hydrocolloid band used as a medical wet band.

6. The band for surgical wound suture of claim 1, wherein a lower surface of the first handle has an adhesive layer and a protective sheet.

* * * * *